(12) United States Patent
Sollid et al.

(10) Patent No.: US 10,677,794 B2
(45) Date of Patent: Jun. 9, 2020

(54) DETECTION OF GLUTEN-SPECIFIC T-CELLS

(71) Applicant: OSLO UNIVERSITETSSYKEHUS HF, Oslo (NO)

(72) Inventors: Ludvig Sollid, Bekkestua (NO); Shuo-wang Qiao, Hvalstad (NO); Asbjorn Christophersen, Oslo (NO); Knut E. A. Lundin, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 543 days.

(21) Appl. No.: 14/891,001

(22) PCT Filed: May 14, 2014

(86) PCT No.: PCT/IB2014/001803
§ 371 (c)(1),
(2) Date: Nov. 13, 2015

(87) PCT Pub. No.: WO2014/191839
PCT Pub. Date: Dec. 4, 2014

(65) Prior Publication Data
US 2016/0109443 A1    Apr. 21, 2016

Related U.S. Application Data
(60) Provisional application No. 61/823,072, filed on May 14, 2013.

(51) Int. Cl.
*G01N 33/564* (2006.01)
*G01N 33/50* (2006.01)

(52) U.S. Cl.
CPC ......... *G01N 33/564* (2013.01); *G01N 33/505* (2013.01); *G01N 33/5091* (2013.01);
(Continued)

(58) Field of Classification Search
CPC .............. G01N 33/564; G01N 33/505; G01N 33/5091; G01N 2333/70546;
(Continued)

(56) References Cited

U.S. PATENT DOCUMENTS
2010/0168390 A1*  7/2010  Brix .................. B82Y 5/00
                                                    530/350

FOREIGN PATENT DOCUMENTS
WO       01/25793        4/2001
WO       02/072631       9/2002
WO       2010/037397     4/2010

OTHER PUBLICATIONS

Raki et al. Tetramer visualization of gut-homing gluten-specific T cells in the peripheral blood of celiac disease patients. PNAS 104 (8): 2831-2836 (Feb. 20, 2007).*

(Continued)

*Primary Examiner* — Gailene Gabel
(74) *Attorney, Agent, or Firm* — Casimir Jones S.C.; J. Mitchell Jones

(57) ABSTRACT

The present invention relates to compositions and methods for visualizing disease-specific T-cells. In particular, the present invention relates to compositions and methods for use in the diagnosis, monitoring of progression, monitoring of response to therapy, and selection of patients for therapy of autoimmune diseases characterized by selective expansion of disease-specific effector memory T-cells.

16 Claims, 9 Drawing Sheets

Specification includes a Sequence Listing.

(52) U.S. Cl.
CPC ............ *G01N 2333/70514* (2013.01); *G01N 2333/70546* (2013.01); *G01N 2800/06* (2013.01); *G01N 2800/24* (2013.01); *G01N 2800/26* (2013.01); *G01N 2800/60* (2013.01)

(58) Field of Classification Search
CPC ..... G01N 2333/70514; G01N 2800/06; G01N 2800/24; G01N 2800/26; G01N 2800/60
See application file for complete search history.

(56) References Cited

OTHER PUBLICATIONS

Soliid et al. Nomenclature and listing of celiac disease relevant gluten T-cell epitopes restricted by HLA-DQ molecules. Immunogenetics 64:455-460 (Feb. 10, 2012).*

Brottveit et al. Assessing Possible Celiac Disease by an HLA-DQ2-giadin Tetramer Test. The American Journal of Gastroentorology . 106: 1318-1324. (Jul. 2011).*

AGA Institute Medical Position Statement on the Diagnosis and Management of Celiac Disease' Gastroenterology vol. 131, 2006, pp. 1977-1980.

Akue et al. "Derivation and Maintenance of Virtual Memory CD8 T Cells." Journal of Immunology, vol. 188, 2012, pp. 2516-2523.

Bodd et al. "HLA-DQ2-restricted gluten-reactive T cells produce IL-21 but not IL-17 or IL-22," Mucosal Immunology, vol. 3, No. 6, pp. 594-601, 2010.

Dickey et al.."Reliance on serum endomysial antibody testing underestimates the true prevalence of coeliac disease by one fifth", Scand J Gastroenterol vol. 35, 2000, pp. 181-183.

Di Niro et al., "Abundance and Unique Repertoire of Plasma Cells Secreting IgA Autoantibodies to Transglutaminase 2 in the Intestinal Lesion of Celiac Disease." Nature medicine 18.3 (2012): 441-445.

Green, "Celiac disease: how many biopsies for diagnosis" Gastrointest Endosc vol. 67, 2008, pp. 1088-1090.

Halstensen et al.,"Activated T lymphocytes in the celiac lesion: non-proliferative activation (CD25) of CD4+ alpha/beta cells in the lamina propria but proliferation (Ki-67) of alpha/beta and gamma/delta cells in the epithelium" Eur J Immunol vol. 23, 1993, pp. 505-510.

Haluszczak et al. "The antigen-specific CD8+ T cell repertoire in unimmunized mice includes memory phenotype cells bearing markers of homeostatic expansion" The Journal of Experimental Medicine vol. 206, 2009, pp. 435-448.

Harrington et al., "Memory CD4 T cells emerge from effector T-cell progenitors",Nature vol. 452, 2008, pp. 356-360.

Jabri et al., "Tissue-mediated control of immunopathology in coeliac disease" Nat Rev Immunol 2009;9:858-70.

Kaukinen et al., "Celiac disease without villous atrophy: revision of criteria called for." Dig Dis Sci vol. 46, 2001, pp. 879-887.

Kurppa et al."Diagnosing Mild Enteropathy Celiac Disease: A Randomized, Controlled Clinical Study" Gastroenterology vol. 136, 2009, pp. 816-823.

Kwok et al., "Frequency of Epitope Specific Naïve CD4+ T Cells Correlates with Immunodominance in the Human Memory Repertoire." Journal of immunology 188.6 (2012): 2537-2544.

Legoux et al.; Impact of T Cell Receptor Reactivity and HLA Phenotype on Naive CD8 T Cell Frequency in Humans. J Immunol. 2010. 184, 6731-8.

Lundin et al., Gliadin-Specific, HLA-DQ, "Restricted T Cells Isolated from the Small Intestinal Mucosa of Celiac Disease Patients." The Journal of Experimental Medicine 178.1 (1993): 187-196.

Lundin et al., "T cells from the small intestinal mucosa of a DR4, DQ7/DR4, DQ8 celiac disease patient preferentially recognize gliadin when presented by DQ8"Hum Immunol. Dec. 1994;41(4):285-91.

Marsh "Gluten, major histocompatibility complex, and the small intestine. A molecular and immunobiologic approach to the spectrum of gluten sensitivity ('celiac sprue')", Gastroenterology vol. 102, 1992, pp. 330-354.

Meresse et al., "1.Coordinated Induction by IL 15 of a TCR-Independent NKG2D Signaling Pathway Converts CTL into Lymphokine-Activated Killer Cells in Celiac Disease", Immunity vol. 21, 2004, pp. 357-366.

Molberg et al.,Gliadin Specific, HLA DQ2-Restricted T Cells are Commonly Found in Small Intestinal Biopsies from Coeliac Disease Patients, but not from Controls. Scandinavian Journal of Immunology, 46: 103-109, (2012).

Olaussen et al., "Reduced Chemokine Receptor 9 on Intraepithelial Lymphocytes in Celiac Disease Suggests Persistent Epithelial Activation" Gastroenterology vol. 132, 2007, pp. 2371-2382.

Pais et al., "How many duodenal biopsy specimens are required to make a diagnosis of celiac disease?"Gastrointest Endosc vol. 67, 2008, pp. 1082-1087.

Pepper et al., "Different routes of bacterial infection induce long-lived TH1 memory cells and short-lived TH17 cells", Nat Immunol 2010;11:83-9.

Rudd et al., "Nonrandom Attrition of the Naive CD8+ T-Cell Pool with Aging Governed by T-Cell receptor:pMHC Interactions." Proc Natl Acad Sci U S A vol. 108, 2011, pp. 13694-13699.

Sollid et al., "Is celiac disease an autoimmune disorder?" Curr Opin Immunol vol. 17, 2005, pp. 595-600.

Su et al.,"Virus-Specific CD4+ Memory Phenotype T Cells Are Abundant in Unexposed Adults." Immunity 38.2 (2013): 373-383.

Sulkanen et al., "Tissue transglutaminase autoantibody enzyme-linked immunosorbent assay in detecting celiac disease", Gastroenterology vol. 115, 1998, pp. 1322-1328.

Wahab et al., "Histologic Follow-up of People With Celiac Disease on a Gluten-Free DietSlow and Incomplete Recovery", Am J Clin Pathol vol. 18, 2002, pp. 459-630.

Weir et al., Am J Gastroentero, "Variability of Histopathological Changes in Childhood Celiac Disease" vol. 105, 2010, pp. 207-212.

International Search Report, International Patent Application No. PCT/IB2014/001803 dated Jan. 22, 2015.

Anderson et al., "In vivo antigen challenge in celiac disease identifies a single transglutaminase-modified peptide as the dominant A-gliadin T-cell epitope", Nature Medicine, vol. 6, No. 3,pp. 337-342, Mar. 2000.

Arentz-Hansen et al., "The intestinal T cell response to alpha-gliadin in adult celiac disease is focused on a single deamidated glutamine targeted by tissue transglutaminase", J Exp Med. Feb. 21, 2000;191(4):603-12.

Batard et al, "Dextramers: new generation of fluorescent MHC class I/peptide multimers for visualization of antigen-specific CD8+ T cells", J Immunol Methods. Mar. 20, 2006;310(1-2):136-48. Epub Feb. 17, 2006.

Brottveit et al., "Assessing possible celiac disease by an HLA-DQ2-gliadin Tetramer Test", Am J Gastroenterol. Jul. 2011;106(7):1318-241.

Jensen et al., "Gliadin-specific T cell responses in peripheral blood of healthy individuals involve T cells restricted by the coeliac disease associated DQ2 heterodimer" \, Scand J Immunol. Jul. 1995;42(1):166-70.

Pepper et al., "Origins of CD4+ effector and central memory T cells", Nat Immunol 2011, vol. 12(6) :467-471.

* cited by examiner

DETECTION OF GLUTEN-SPECIFIC T-CELLS

CROSS-REFERENCE TO RELATED APPLICATION

This application is a 371 U.S. National Phase Entry of pending International Patent Application No. PCT/IB2014/001803, International Filing Date May 14, 2014, which claims priority to U.S. Provisional Patent Application No. 61/823,072, filed May 14, 2013, the contents of which are incorporated by reference in their entireties.

FIELD OF THE INVENTION

The present invention relates to compositions and methods for visualizing disease-specific T-cells. In particular, the present invention relates to compositions and methods for use in the diagnosis, monitoring of progression, monitoring of response to therapy, and selection of patients for therapy of autoimmune diseases characterized by selective expansion of disease-specific effector memory T-cells.

BACKGROUND OF THE INVENTION

Celiac disease (CD) is defined as intolerance to proline- and glutamine-rich gluten proteins of wheat, barley and rye (Koning, Semin Immunopathol), that can cause chronic inflammation in the small intestine (Ludvigsson et al., Gut 2012; 62:43-52). CD patients may present with fatigue, malabsorption, anemia, osteoporosis or neurological signs. The disease is often detected after demonstration of autoantibodies to the enzyme transglutaminase 2 (TG2) (Green et al., N Engl J Med 2007; 357:1731-43). In children the diagnosis can be made without gastroduodenoscopy if the TG2 antibody titer in blood is highly elevated (Husby et al., J Pediatr Gastroenterol Nutr 2012; 54:136-60). In adults however, duodenal biopsy examination and detection of typical histological changes remains a diagnostic premise (AGA Institute Medical Position Statement on the Diagnosis and Management of Celiac Disease. Gastroenterology 2006; 131:1977-80).

Heterogeneity in the clinical appearance leaves the diagnosis of CD uncertain in many cases. Several patients fail to be referred to gastroduodenoscopy because of false negative antibody tests. Autoantibodies can be present in tissues only but not in blood (Dickey et al., Scand J Gastroenterol 2000; 35:181-3; Kurppa et al., J Pediatr Gastroenterol Nutr 2012; 54:387-91). Frequently, patients present with specific antibody-titers but minor or no changes in the duodenal mucosa (Paparo F et al., Am J Gastroenterol 2005; 100:2294-8). As the small intestine architecture deteriorates gradually by gluten exposure in CD patients (Marsh M N, Gastroenterology 1992; 102:330-54), some are diagnosed later when gastroduodenoscopy is repeated (Kurppa K, et al., Gastroenterology 2009; 136:816-23). Gastroduodenoscopy can only be accomplished by trained physicians. Compared to blood sample-based diagnostic methods, a gastroduodenoscopy is also more invasive and involves longer post intervention surveillance. Some patients also benefit from a gluten-free diet (GFD) although the criteria for diagnosis (AGA Institute Medical Position Statement on the Diagnosis and Management of Celiac Disease. Gastroenterology 2006; 131:1977-80) are not fulfilled (Kurppa K, et al., Gastroenterology 2009; 136:816-23; Kaukinen et al., Dig Dis Sci 2001; 46-869-87).

Improved compositions and methods for diagnosing CD are needed that clarify diagnosis. Development of a biopsy independent diagnostic test for CD is beneficial both for the patient and for patient care costs.

SUMMARY OF THE INVENTION

The present invention relates to compositions and methods for visualizing disease-specific T-cells. In particular, the present invention relates to compositions and methods for use in the diagnosis, monitoring of progression, monitoring of response to therapy, and selection of patients for therapy of autoimmune diseases characterized by selective expansion of disease-specific effector memory T-cells.

Embodiments of the present invention provides compositions, systems, uses, and methods of identifying a disease-specific T-cell response, comprising: a) contacting a blood sample from a subject with a multimeric polypeptide comprising a plurality of disease epitope peptides (e.g., bound to a solid support); b) detecting the presence, absence, or level of CD4+ T-cells binding the disease-specific multimeric polypeptide (e.g., by separating CD4+ T-cells from the bound T-cells using an antibody specific for CD4+ T-cells to generate disease specific CD4+ T-cells); and c) identifying the subject as having the disease when the disease specific CD4+ T-cells are present or present above a threshold level in the sample. In some embodiments, the method further comprises the steps of: separating the CD4+ T-cells by their expression of organ-homing proteins (e.g., including, but not limited to integrins or chemokine receptors such as integrin α4β7 or chemokine receptor type 9 for gut-homing and equivalent homing-receptors for other organs); separating the CD4+ T-cells by their expression of T-cell receptors (TCR) using disease-associated α- and/or β-chains); and quantifying and monitoring the CD4+ T-cells or phenotypes of CD4+ T-cells expressing these certain disease-related TCR α- and/or β-chains. In some embodiments, the method comprises the steps of: separating the CD4+ T-cells into Naïve ($T_N$), central memory ($T_{CM}$) and effector memory ($T_{EM}$) CD4+ T-cells; and quantifying the $T_N$, $T_{CM}$, and $T_{EM}$ CD4+ T-cells. In some embodiments, the steps of separating CD4+ T-cells from the bound T-cells using an antibody specific for CD4+ T-cells and separating said CD4+ T-cells into $T_N$, $T_{CM}$ and $T_{EM}$ CD4+ T-cells is done by flow cytometry. In some embodiments, the solid support is a bead. In some embodiments, the disease epitope is present on the solid support as a tetramer. In some embodiments, the disease epitope is an DQ epitope (e.g., those described in Sollid et al., Immunogenetics 2012; 64:455-460; herein incorporated by reference in its entirety and those described herein). Examples include, but are limited to, DQ2.5 epitopes such as DQ2.5-glia-α1a, DQ2.5-glia-α1b, DQ2.5-glia-α2, DQ2.5-glia-α3, DQ2.5-glia-γ1, DQ2.5-glia-γ2, DQ2.5-glia-γ3, DQ2.5-glia-γ4a, DQ2.5-glia-γ4b, DQ2.5-glia-γ4c, DQ2.5-glia-γ4d, DQ2.5-glia-γ5, DQ2.5-glia-ω1, DQ2.5-glia-ω2, DQ2.5-glut-L1, DQ2.5-glut-L2, DQ2.5-hor-1, DQ2.5-hor-2, DQ2.5-hor-3, DQ2.5-sec-1, DQ2.5-sec-2, DQ2.5-ave-1 or DQ2.5-ave-2; or DQ2.2 epitopes such as DQ2.2-glut-L1, DQ2.2-glia-α1 or DQ2.2-glia-α2; or DQ8 epitopes such as DQ8-glia-α1, DQ8-glia-γ1a, DQ8-glia-γ1b or DQ8-glut-H1. In some embodiments, the method further comprises the step of assaying the T-cells for expression of integrin-β7. In some embodiments, expression of integrin-β7 and/or CD38 (e.g., in combination with a $T_{EM}/T_N$ ratio greater than one) is indicative of a disease-specific T-cell response in the subject. In some embodiments, the disease is an autoimmune disease characterized by expansion of effector memory T-cells. Examples include, but are not limited to, acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behçet's disease, Berger's disease, Bickerstaffs encephalitis, Blau syndrome, bullous pemphigoid, Castleman's disease, Celiac disease, chronic inflammatory demyelinating polyneuropathy, chronic recurrent multifocal osteomyelitis, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrom, cutaneous leukocytoclastic angiitis, Dego's disease, dermatitis herpetiformis, dermatomyositis, diabetes mellitus type 1, diffuse cutaneous systemic sclerosis, Dressler's syndrome, lupus erythematosus, eczema, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, Goodpasture's syndrome, Graves' disease, Guillain-Barré syndrome, Hashimoto's encephalopathy, Hashimoto's thyroiditis, Henoch-Schonlein purpura, Herpes gestationis aka gestational pemphigoid, Hughes-Stovin syndrome, hypogammaglobulinemia, idiopathic inflammatory demyelinating diseases, idiopathic pulmonary fibrosis, idiopathic thrombocytopenic purpura, inclusion body myositis, chronic inflammatory demyelinating polyneuropathy, Lambert-Eaton myasthenic syndrome, leukocytoclastic vasculitis, lichen planus, lichen sclerosus, linear IgA disease (LAD), lupoid hepatitis aka autoimmune hepatitis, Majeed syndrome, Ménière's disease, microscopic polyangiitis, mixed connective tissue disease, Mucha-Habermann disease aka pityriasis lichenoides et varioliformis acuta, myasthenia gravis, myositis, neuromyelitis optica (also Devic's disease), occular cicatricial pemphigoid, Ord's thyroiditis, palindromic rheumatism, PANDAS (pediatric autoimmune neuropsychiatric disorders associated with streptococcus), paraneoplastic cerebellar degeneration, paroxysmal nocturnal hemoglobinuria, Parry Romberg syndrome, Parsonage-Turner syndrome, pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, psoriasis, psoriatic arthritis, pyoderma gangrenosum, pure red cell aplasia, Rasmussen's encephalitis, relapsing polychondritis, Reiter's syndrome, retroperitoneal fibrosis, rheumatoid arthritis, rheumatic fever, Schmidt syndrome, Schnitzler syndrome, Scleritis, serum Sickness, Sjögren's syndrome, spondyloarthropathy, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease different from mixed connective tissue disease, undifferentiated spondyloarthropathy, urticarial vasculitis, vasculitis, and Wegener's granulomatosis. In some embodiments, the disease is celiac disease (CD). In some embodiments, the sample is from a subject that has not been exposed to gluten (e.g., for at least a day, week, month, or longer) prior to the sample being obtained. In some embodiments, an increase in CD4+ $T_{EM}$ cells is indicative of CD in said subject. In some embodiments, an increased number of CD4+ $T_{EM}$ cells is indicative of severe CD with, for example, duodenal changes. In some embodiments, the method further comprises the step of calculating the ratio of CD4+ $T_{EM}$- cells to CD4+ $T_N$ cells and establishing a threshold value of the ratio that indicates disease. In some embodiments, a ratio of greater than the threshold level (e.g., one) is indicative of an immune response to the disease epitope. In some embodiments, the presence of greater a threshold level of CD4+ $T_{EM}$ cell per million total CD4+ T-cells (e.g., one) is indicative of disease in the subject.

Additional embodiments are described herein.

DEFINITIONS

Figure 1:
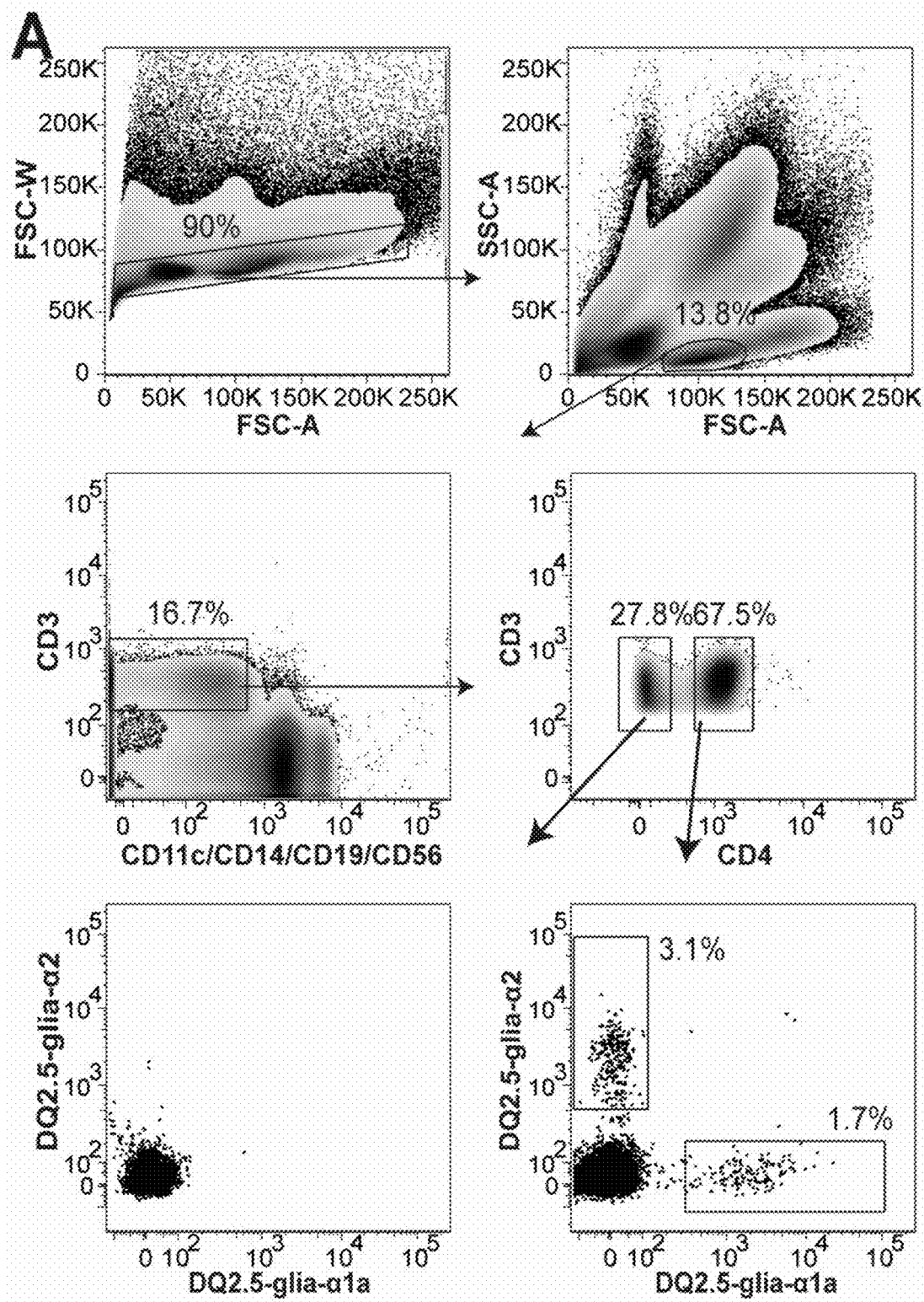
FIG. 1 shows flow cytometric density plots and dot plots illustrating the gating strategy for relevant tetramer-binding cells. (A) Gating was done on mononuclear cells→lymphocytes→CD3+ cells→CD4+ cells. (B) Tetramer+CD4+ T cells were subdivided by CD62L- and CD45RA-staining into $T_{EM}$ cells (double negative), $T_N$ (double positive), $T_{CM}$ (CD62L+ and CD45RA-). Tetramer-binding HLA-DQ2.5+ cells were identified in controls, untreated-(UCD) and treated CD patients (TCD).
Figure 1:
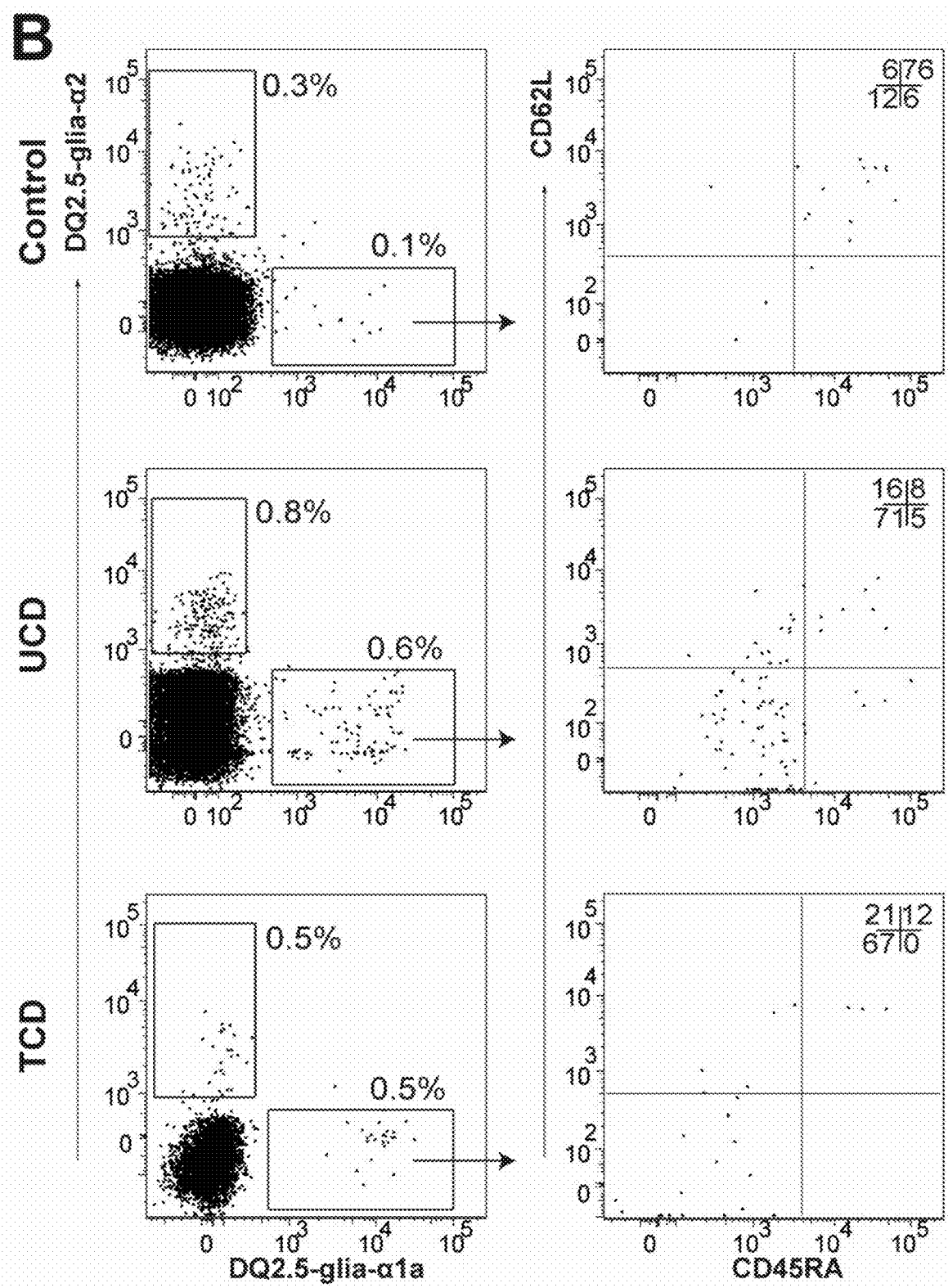

A used herein, the term "immune response" refers to a response by the immune system of a subject. For example, immune responses include, but are not limited to, a detectable alteration (e.g., increase) in Toll-like receptor activation, lymphokine (e.g., cytokine (e.g., Th1, Th2, $T_{REG}$, or Th17 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll-like receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) and/or portion or component thereof (e.g., a protein antigen)) that is capable of eliciting an immune response in a subject. In some embodiments, immunogens elicit immunity against the immunogen (e.g., microorganism (e.g., pathogen or a pathogen product)).

The term "sample" as used herein is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the term "peptide" refers to a polymer of two or more amino acids joined via peptide bonds or modified peptide bonds. As used herein, the term "dipeptides" refers to a polymer of two amino acids joined via a peptide or modified peptide bond.

As used herein, the term "purified" or "to purify" refers to the removal of contaminants from a sample. For example, antigens are purified by removal of contaminating proteins. The removal of contaminants results in an increase in the percent of antigen (e.g., antigen of the present invention) in the sample.

DETAILED DESCRIPTION OF THE INVENTION

The present invention relates to compositions and methods for visualizing disease-specific T-cells. In particular, the present invention relates to compositions and methods for use in the diagnosis, monitoring of progression, monitoring of response to therapy, and selection of patients for therapy of autoimmune diseases characterized by selective expansion of disease-specific effector memory T-cells.

The T-cell response to gluten is important both in the development and in the maintenance of CD. This is supported by the strong disease association with certain HLA-DQ alleles (HLA-DQ2.5, HLA-DQ2.2, and HLA-DQ8) and the detection of gluten-reactive CD4+ T cells restricted by the disease-associated HLA alleles in the gut mucosa of CD patients but not of healthy controls (Lundin et al., J Exp Med 1993; 178:187-96; Lundin et al., Hum Immunol 1994; 41:285-91; Molberg et al., Scand J Immunol 1997; 46:103-9; Bodd et al., Gastroenterology; 2012 142:552-61). The T-cell response has not directly been applicable in CD diagnosis despite its key-role in the disease pathogenesis. Whereas many aspects of the mucosal T cells have been elucidated, less is known about the T-cell repertoire in peripheral blood in celiac disease. One previous study showed that gluten-specific, HLA-DQ2.5-restricted, CD4+ T-cell clones could be cultured from peripheral blood of healthy individuals (Jensen et al., Scand J Immunol 1995; 42:166-70). This in vitro protocol is demanding and gives little information on the magnitude of the T-cell response. Gluten-specific CD4+ T cells were also detected in peripheral blood mononuclear cells (PBMC) using enzyme-linked immunospot- or tetramer-based assays. However, this was only possible in treated CD patients (TCD) (accordingly patients on a GFD), after a short consumption of wheat-containing food. This procedure known as "gluten-challenge," gave a boost of gluten-specific T cells into the blood (Anderson et al., Nat Med 2000; 6:337-42; Raki et al., Proc Natl Acad Sci USA 2007; 104:2831-6). Notably, gluten-specific T cells were not detectable above background in healthy controls, untreated CD patients (UCD) or TCD without gluten-challenge or long-term in vitro culture, in these studies (Brottveit et al., Am J Gastroenterol 2011; 106:1318-24; A. Camarca et al., Clinical and Experimental Immunology 2012; 169:129-136).

Experiments described herein increased the sensitivity for detection of gluten-reactive T cells in blood from HLA DQ2.5+ individuals by performing bead-enrichment of cells binding DQ2.5 tetramers representing two immunodominant gliadin epitopes (Arentz-Hansen et al., J Exp Med 2000; 191:603-12). HLA-DQ8+ individuals (DQ8 tetramers representing immunodominant and relevant gliadin epitopes) and HLA-DQ2.2+ individuals (DQ2.2 tetramers representing immunodominant and relevant gliadin and glutenin epitopes) were also included in experiments to cover the three HLA-groups related to increased risk for CD and thereby >99% of all potential CD patients. Relevant CD4+ T cells were tracked and subdivided into three different phenotypes: Naïve ($T_N$), central memory ($T_{CM}$) and effector memory $T_{EM}$. $T_N$ are preimmune cells that can respond with clonal expansion and differentiate into memory T cells if encountering a corresponding antigen. Memory T cells are categorized by their expression of homing markers and cytokine production into $T_{EM}$ that act at the site of inflammation and $T_{CM}$ that can migrate to lymphoid tissues (Pepper et al., Nat Immunol 2011; 12:467-71).

Significantly more gluten-reactive CD4+ TEM cells were observed in UCD and TCD patients compared to controls and a persistent immune-response to gluten in all TCD. These cells were gut-homing, and were found in larger numbers in CD patients with severe duodenal changes compared to CD patients with normal mucosa. There was also significantly more gluten-reactive CD4+ $T_{EM}$ in blood from CD patients with severe duodenal changes compared to CD patients with normal mucosa. This protocol gives access to gluten-reactive T cells of different phenotypes in peripheral blood from both diseased and healthy individuals. The results of the experiments described herein demonstrate that this T cell based ex-vivo assay finds use in the diagnosis of CD and other disorders related to T-cell responses (e.g., to HLA-DQ2.5, HLA-DQ-2.2, and HLA-DQ-8 peptides).

Accordingly, embodiments of the present invention provide compositions and methods for diagnosing T-cell mediated diseases (e.g., CD) by identifying and quantifying CD4+ T-cells that binds to disease specific antigens. Embodiments of the present invention are exemplified with the detection of T-cells that bind to CD specific epitopes (e.g., DQ2.5, DQ2.2 and DQ8 epitopes).

However, the present invention is not limited to the detection of CD specific T-cells or providing a diagnosis and/or prognosis of CD. The compositions and methods described herein find use in the diagnosis and prognosis of any number of T-cell mediated diseases where a specific epitope has been identified. Examples include, but are not limited to, acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behçet's disease, Berger's disease, Bickerstaffs encephalitis, Blau syndrome, bullous pemphigoid, Castleman's disease, Celiac disease, chronic inflammatory demyelinating polyneuropathy, chronic recurrent multifocal osteomyelitis, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrom, cutaneous leukocytoclastic angiitis, Dego's disease, dermatitis herpetiformis, dermatomyositis, diabetes mellitus type 1, diffuse cutaneous systemic sclerosis, Dressler's syndrome, lupus erythematosus, eczema, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, Goodpasture's syndrome, Graves' disease, Guillain-Barré syndrome, Hashimoto's encephalopathy, Hashimoto's thyroiditis, Henoch-Schonlein purpura, Herpes gestationis aka gestational pemphigoid, Hughes-Stovin syndrome, hypogammaglobulinemia, idiopathic inflammatory demyelinating diseases, idiopathic pulmonary fibrosis, idiopathic thrombocytopenic purpura, inclusion body myositis, chronic inflammatory demyelinating polyneuropathy, Lambert-Eaton myasthenic syndrome, leukocytoclastic vasculitis, lichen planus, lichen sclerosus, linear IgA disease (LAD), lupoid hepatitis aka autoimmune hepatitis, Majeed syndrome, Ménière's disease, microscopic polyangiitis, mixed connective tissue disease, Mucha-Habermann disease aka pityriasis lichenoides et varioliformis acuta, myasthenia gravis, myositis, neuromyelitis optica (also Devic's disease), ocular cicatricial pemphigoid, Ord's thyroiditis, palindromic rheumatism, PANDAS (pediatric autoimmune neuropsychiatric disorders associated with streptococcus), paraneoplastic cerebellar degeneration, paroxysmal nocturnal hemoglobinuria, Parry Romberg syndrome, Parsonage-Turner syndrome, pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, psoriasis, psoriatic arthritis, pyoderma gangrenosum, pure red cell aplasia, Rasmussen's encephalitis, relapsing polychondritis, Reiter's syndrome, retroperitoneal fibrosis, rheumatoid arthritis, rheumatic fever, Schmidt syndrome, Schnitzler syndrome, Scleritis, serum Sickness, Sjögren's syndrome, spondyloarthropathy, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease different from mixed connective tissue disease, undifferentiated spondyloarthropathy, urticarial vasculitis, vasculitis, and Wegener's granulomatosis.

The compositions and methods of embodiments of the present invention provide the advantage of being able to detect disease specific T-cells in subject that have not been exposed to the antigen (e.g., gluten). Thus, in some embodiments, subjects undergoing analysis have not consumed gluten for at least a day, several days, a week, several weeks, a month, or several months prior to the sample being obtained.

The present invention is not limited to a particular sample. In some embodiments, the sample is blood, lymph, or blood products (e.g. buffy coat). In some embodiments, the sample is enriched for T-cells prior to performing the methods described herein. For example, in some embodiments, peripheral blood mononuclear cells (PBMC) are isolated from blood or blood products (e.g., using centrifugation or filtration).

In some embodiments, blood samples from a patient are first enriched for T-cells that bind to a disease specific epitope. In some embodiments, a solid support (e.g., bead or particle) is functionalized with peptides comprising the disease specific epitope. In some embodiments, a plurality of peptides, each of which comprises at least one disease specific epitope, are attached to the solid support. In some embodiments, tetramers of epitopes are utilized, although other numbers are specifically contemplated. After T-cells have bound to the epitopes on the solid support, the solid supports are separated from the remaining sample (e.g., via a tag or label on the solid support or via magnetic supports and magnet). This generates a population of T-cell with specific affinity for the disease epitope.

In some embodiments, T-cells are next separated into specific populations of T-cells using specific reagents (e.g., antibodies) and separation methods (e.g., flow cytometry), although other methods are specifically contemplated. In some embodiments, T-cells are detected without separation. In some embodiments, CD4+ T-cells are separated from the remaining population of disease specific epitope binding T-cells. In some embodiments, CD4+ T-cells are separated into naïve ($T_N$), central memory ($T_{CM}$) and effector memory ($T_{EM}$) CD4+ T-cells. In some embodiments, CD4+ T-cells are separated by their expression of organ-homing proteins. In some embodiments, CD4+ T-cells are separated by their expression of disease-related TCR. In some embodiments, methods of isolating or separating CD4+ T cells include, but are not limited to, CD4+ isolation and/or enrichment kits supplied e.g., by Stem Cell Technologies, Miltenyi Biotec, Life Technologies and BD Biosciences. In some embodiments, the number of T-cells in each category is quantified.

In some embodiments, the ratio of $T_{EM}/T_N$ cells (or other ratios) is calculated. In some embodiments, the CD4+ T cells are further analyzed for expression of the gut-homing marker integrin-$\beta 7$ and activation markers such as CD38.

In some embodiments, the levels or ratios of specific classes of disease specific T-cells is utilized to provide diagnostic, screening, disease progression, treatment response, selection of patients for treatment, or prognostic information. For example, in some embodiments, a high number (e.g., greater than 1 per million) of $T_{EM}$ cells or a specific $T_{EM}/T_N$ ratio (e.g., greater than one) is indicative of a diagnosis or CD or an increased level or severity of CD. In some embodiments the $T_{EM}/T_N$ ratio is combined with the expression of integrin-$\beta 7$ to provide a composite score with improved ability to differentiate between disease-associated and non-disease-associated tetramer-positive cells. In some embodiments, the ratio or level of $T_{EM}$ cells useful for a particular application (e.g., diagnosis, prognosis, response to treatment, etc.) is empirically determined by comparing the level or ratio of $T_{EM}$ cells among subjects diagnosed with a particular T-cell mediated disorder or undergoing a particular treatment for a T-cell mediated disorder.

The present invention also relates to a kit comprising reagents useful, necessary, or sufficient for diagnostic, medical or scientific purposes. For example, in some embodiments, the reagents comprise antibodies, peptides comprising disease specific epitopes, solid supports, controls, and instruction.

The diagnostic kits may further comprise any reagent or media necessary, sufficient or useful to perform analyses, such as solid support capture, flow cytometry, sample purification and the like.

In some embodiments, the kits of the present invention include a means for containing the reagents in close confinement for commercial sale such as, e.g., injection or blow-molded plastic containers into which the desired reagent are retained. Other containers suitable for conducting certain steps of the disclosed methods also may be provided.

The present invention also provides methods and materials to assist medical or research professionals in determining whether or not a mammal has a T-cell mediated disease (e.g., CD). Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the ratio or level of particular T-cells in a sample, and (2) communicating information about the ratio to that professional, for example.

After the level (score, frequency) of particular markers in a blood, serum, or plasma sample is reported, a medical professional can take one or more actions that can affect patient care. For example, a medical professional can record the results in a patient's medical record. In some cases, a medical professional can record a diagnosis of a disease, or otherwise transform the patient's medical record, to reflect the patient's medical condition. In some cases, a medical professional can review and evaluate a patient's entire medical record, and assess multiple treatment strategies, for clinical intervention of a patient's condition. In some cases, a medical professional can record a prediction of disease progression. In some cases, a medical professional can review and evaluate a patient's entire medical record and assess multiple treatment strategies, for clinical intervention of a patient's condition.

A medical professional can initiate or modify treatment of a disease after receiving information regarding the level (score, frequency) associated with disease specific T-cells in a patient's blood, blood product, serum, or plasma sample. In some cases, a medical professional can compare previous reports and the recently communicated level (score, frequency) of markers, and recommend a change in therapy. In some cases, a medical professional can enroll a patient in a clinical trial for novel therapeutic intervention. In some cases, a medical professional can elect waiting to begin therapy until the patient's symptoms require clinical intervention.

A medical professional can communicate the assay results to a patient or a patient's family. In some cases, a medical professional can provide a patient and/or a patient's family with information regarding disease (e.g., CD), including treatment options, prognosis, and referrals to specialists, e.g., immunologists or gastroenterologists. In some cases, a medical professional can provide a copy of a patient's medical records to communicate assay results to a specialist. A research professional can apply information regarding a subject's assay results to advance disease research. For example, a researcher can compile data on the assay results, with information regarding the efficacy of a drug for treatment of a disease such as CD to identify an effective treatment. In some cases, a research professional can obtain assay results to evaluate a subject's enrollment, or continued participation in a research study or clinical trial. In some cases, a research professional can classify the severity of a subject's condition, based on assay results. In some cases, a research professional can communicate a subject's assay results to a medical professional. In some cases, a research professional can refer a subject to a medical professional for clinical assessment of disease, and treatment thereof. Any appropriate method can be used to communicate information to another person (e.g., a professional). For example, information can be given directly or indirectly to a professional. For example, a laboratory technician can input the assay results into a computer-based record. In some cases, information is communicated by making a physical alteration to medical or research records. For example, a medical professional can make a permanent notation or flag a medical record for communicating a diagnosis to other medical professionals reviewing the record. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

It is noted that a single sample can be analyzed for one disease specific T-cell or for multiple disease specific T-cells.

In some embodiments, the methods disclosed herein are useful in monitoring the treatment of disease (e.g., CD). For example, in some embodiments, the methods may be performed immediately before, during and/or after a treatment to monitor treatment success. In some embodiments, the methods are performed at intervals on disease free patients to ensure treatment success.

The present invention also provides a variety of computer-related embodiments. Specifically, in some embodiments the invention provides computer programming for analyzing and comparing levels or rations of disease specific T-cells in a sample obtained from a subject.

In some embodiments, the present invention provides computer programming for analyzing disease specific T-cell levels from a sample taken at least two different time points. In some embodiments, the first pattern may be indicative of a pre-disease condition and/or low risk condition and/or progression to disease or more advanced disease. In such embodiments, the comparing provides for monitoring of the progression of the condition from the first time point to the second time point.

In yet another embodiment, the invention provides computer programming for analyzing and comparing levels or ratios of disease specific T-cells to obtain differential diagnosis between an aggressively disease and a less aggressive disease (e.g., the marker pattern provides for staging and/or grading of the disease).

The methods and systems described herein can be implemented in numerous ways. In one embodiment, the methods involve use of a communications infrastructure, for example the internet. Several embodiments of the invention are discussed below. It is also to be understood that the present invention may be implemented in various forms of hardware, software, firmware, processors, distributed servers (e.g., as used in cloud computing) or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of hematological neoplasm-specific marker detection results from a sample). This information received can be stored at least temporarily in a database, and data analyzed in comparison to a library of marker patterns known to be indicative of the presence or absence of a pre-cancerous condition, or known to be indicative of a stage and/or grade of hematological cancer.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In some embodiments, all or a portion of the input data and/or all or a portion of the output data (e.g., usually at least the library of the pattern of hematological neoplasm-specific marker detection results known to be indicative of the presence or absence of a pre-cancerous condition) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where detected marker data for a sample obtained from a subject is to be input by a user (e.g., a technician or someone performing the assays)) and transmitted to a remote site to a second computer processor for analysis, where the first and second computer processors are connected by a network, e.g., via an intranet or internet). The system can also include a user component(s) for input; and a reviewer component(s) for review of data, and generation of reports, including diagnosis or characterization of a disease. Additional components of the system can include a server component(s); and a database(s) for storing data (e.g., as in a database of report elements), or a relational database (RDB) which can include data input by the user and data output. The computer processors can be processors that are typically found in personal desktop computers (e.g., IBM, Dell, Macintosh), portable computers, mainframes, minicomputers, tablet computer, smart phone, or other computing devices.

The input components can be complete, stand-alone personal computers offering a full range of power and features to run applications. The user component usually operates under any desired operating system and includes a communication element (e.g., a modem or other hardware for connecting to a network using a cellular phone network, Wi-Fi, Bluetooth, Ethernet, etc.), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe, or distributed across multiple servers (e.g., as in cloud computing applications) and offers data management, information sharing between clients, network administration and security. The application and any databases used can be on the same or different servers. Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

In certain embodiments, the present invention provides methods for obtaining a subject's risk profile for developing a disease (e.g., CD). In some embodiments, such methods involve obtaining a blood or blood product sample from a subject (e.g., a human at risk for developing a disease; a human undergoing a routine physical examination), detecting the presence, absence, or level of one or more disease specific T-cells in or associated with the blood or blood product sample in the sample, and generating a risk profile for developing a disease (e.g., CD). For example, in some embodiments, a generated risk profile will change depending upon specific markers and detected as present or absent or at defined threshold levels. The present invention is not limited to a particular manner of generating the risk profile. In some embodiments, a processor (e.g., computer) is used to generate such a risk profile. In some embodiments, the processor uses an algorithm (e.g., software) specific for interpreting the presence and absence of specific markers as determined with the methods of the present invention. In some embodiments, the presence and absence of specific markers as determined with the methods of the present invention are imputed into such an algorithm, and the risk profile is reported based upon a comparison of such input with established norms (e.g., established norm for disease or type of disease). In some embodiments, the risk profile indicates a subject's risk for developing a T-cell mediated disease. In some embodiments, the risk profile indicates a subject to be, for example, a very low, a low, a moderate, a high, and a very high chance of developing or re-developing disease or having a poor prognosis (e.g., likelihood of long term survival) from the disease. In some embodiments, a health care provider will use such a risk profile in determining a course of treatment or intervention.

EXPERIMENTAL

The following examples are provided in order to demonstrate and further illustrate certain preferred embodiments and aspects of the present invention and are not to be construed as limiting the scope thereof.

Example 1

Materials and Methods

Subjects

Fifty four individuals acceded to the study. They were all genomically HLA-typed for DQA1 and DQB1 alleles. Only the more common CD-associated HLA-types (DQ2.5=DQA1*05, DQB1*02; DQ2.2=DQA1*02:01, DQB1*02 and DQ8=DQA1*03, DQB1*03:02) are reported. There were 20 UCD, 18 TCD and 16 control individuals (Table 1). Blood was obtained from ten DQ2.5+ controls through the Blood Bank at Oslo University Hospital to which they had donated blood for clinical and research purposes. These individuals were anonymous. No data on diet, biomarkers or their clinical state was available. CD was diagnosed via an exclusion criterion for blood donation. All other participants were patients donating additional blood for research purposes in conjunction to duodenal biopsies and routine clinical follow-up at the Oslo University Hospital. The CD patients were diagnosed according to statements from the American Gastroenterological Association (AGA Institute Medical Position Statement on the Diagnosis and Management of Celiac Disease. Gastroenterology 2006; 131:1977-80). Each TCD had been on GFD for three months or more. The study was approved by the regional ethics committee (S-97201) and all participating individuals gave their informed written consent.

Tetramers

Soluble, biotinylated DQ2.5 (DQA1*05:01, DQB1*02:01) molecules covalently linked with the gluten-derived T-cell epitopes DQ2.5-glia-α1a (QLQPFPQPELPY (SEQ ID NO: 1), underlined 9mer core sequence) or DQ2.5-glia-α2 (PQPELPYPQPE (SEQ ID NO: 2)) were multimerized on PE-labeled (Invitrogen) or APC-labeled (ProZyme) streptavidin (Quarsten et al., J Immunol 2001; 167:4861-8). Cells were incubated with the tetramers (10 µg/ml each) at room temperature for 40 minutes.

Cell Enrichment

Sixty ml citrated buffy coat or 60-110 ml of citrated full blood was obtained from each participant. The buffy coat was an intermediate product before thrombocyte-isolation from initial 450 ml full blood. PBMC was isolated from both full blood and the buffy coat by density gradient centrifugation (Lymphoprep; Axis-Shield). PBMC were further handled in a buffer containing phosphate-buffered saline, 1 mM ethylenediaminetetraacetic acid and 1% human serum. A protocol was used for enrichment of tetramer-binding cells (Moon et al., Immunity 2007; 27:203-13). Briefly, PBMC were counted and incubated with FcR blocking reagent (Miltenyi Biotec) before PE- and APC-conjugated tetramers were added together. The cells were washed in ice-cold buffer and a small fraction was removed for later staining as "pre-enriched sample" before anti-PE- and anti-APC microbeads (Miltenyi Biotec) were added. The cells were washed, re-counted and passed over a magnetized column (MS or LS column, Miltenyi Biotec). Cells that did not bind the column were collected as "depleted cells."

Flow Cytometry

The enriched cells were eluted and all samples were stained at a volume of 25 µl on ice for 20 minutes. They were incubated with the following fluorochrome-labeled antibodies: CD62L-PerCP/Cy5.5, CD14-Pacific blue, CD19-Pacific blue, CD56-Pacific Blue, CD11c-V450, CD4-APC-H7 (all from BD Biosciences), CD45RA-PE-Cy7, CD3-eFluor605 (both from eBioscience). The cells were washed and analyzed on a LSR II (BD Biosciences) or sorted on a FACS Aria I cell sorter (BD Biosciences).

Cells binding the DQ2.5-glia-α1a-tetramer or the DQ2.5-glia-α2-tetramer were identified as relevant if they were CD3+/CD11c−/CD14−/CD19−/CD56−/CD4+. Further, relevant tetramer-binding cells were sub-divided into CD45RA+/CD62L+ cells ($T_N$), CD45RA−/CD62L− cells ($T_{EM}$) and CD45RA−/CD62L+ cells ($T_{CM}$) (FIGS. 1A and B) (Sallusto et al., Nature 1999; 401:708-12) and sorted in tubes depending on their phenotype and tetramer binding.

The frequencies of DQ2.5-glia-α1a- and DQ2.5-glia-α2 specific T cells were calculated by dividing tetramer-binding CD4+ T cells in the enriched sample by the total number of CD4+ T cells in the pre-enriched sample and multiplying this number by 1 million. The total number of CD4+ T cells was given by the ratio of CD4+ T cells in the pre-enriched sample multiplied with counted total PBMC number before enrichment. FlowJo software (Tree Star, Ashland, Oreg.) was used for analysis of flow data.

Culturing and Screening of Sorted Cells

Figure 5:
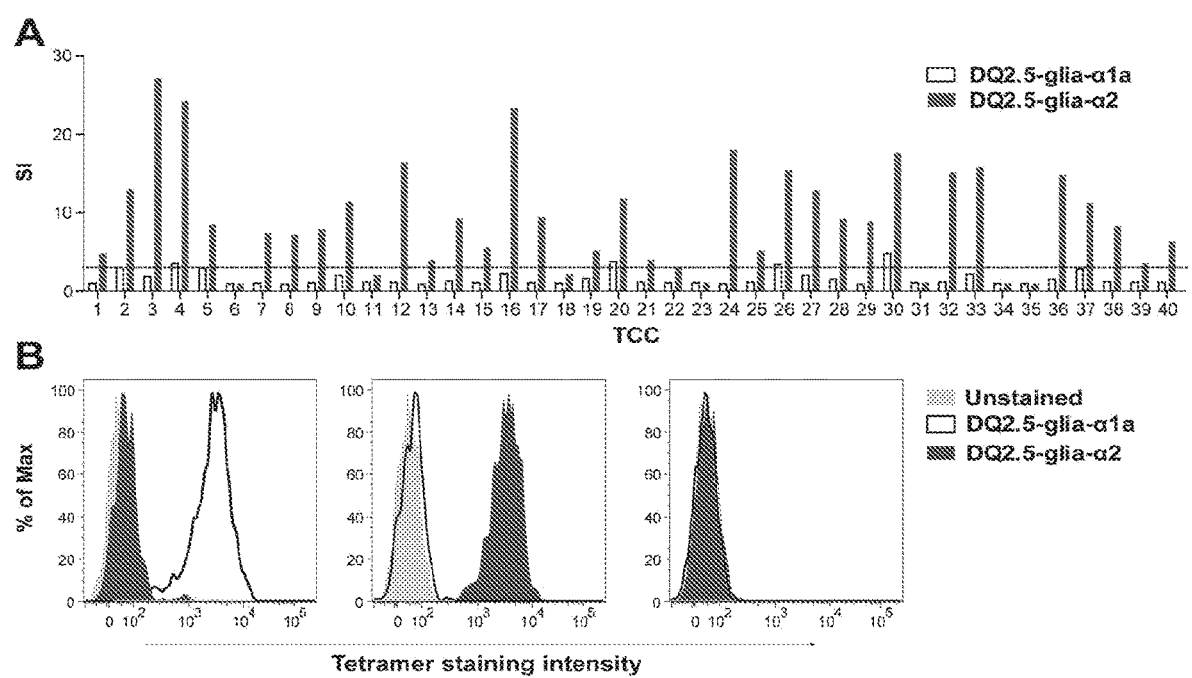
FIG. 5 shows (A) Growing T-cell clones were stimulated with peptides containing the DQ2.5-glia-α1a- or the DQ2.5-glia-α2-epitope. T-cell clones with a stimulation index (SI) >3 were classified as specific. The SI is given by the thymidine incorporation after antigen stimulation/after medium stimulation. (B) Representative flow cytometric plots of T-cell clones depicting what were defined as a specific staining for the DQ2.5-glia-α1a-tetramer (left), the DQ2.5-glia-α2-tetramer (midst) and negative staining for both tetramers (right).

Sorted cells were cloned by limiting dilution and expanded by phytohaemagglutinin, interleukin-2 and interleukin-15 as described in a previous protocol (Molberg et al., Methods Mol Med 2000; 41:105-24). To verify their specificity, growing TCC were tested both in T-cell proliferation assay and by re-staining with PE- or APC-conjugated DQ2.5-glia-α1a- and DQ2.5-glia-α2-tetramers. The tetramer-stained cells were analyzed on a FACS Calibur (BD Biosciences) (FIG. 5). Cells showing a clear shift in staining-intensity with the DQ2.5-glia-α1a-tetramer compared to the DQ2.5-glia-α2-tetramer and the unstained control were identified as specific for the DQ2.5-glia-α1a-peptide, and vice versa.

A protocol was used for antigen-dependent T-cell proliferation (Molberg et al. supra). Briefly, DQ2.5 homozygous EBV-transformed cells (IHW #9023) were used as antigen-presenting cells, presenting the DQ2.5-glia-α1a-epitope peptide (QLQPFPQPELPY (SEQ ID NO: 1), underlined 9mer core sequence) or a peptide containing the DQ2.5-glia-α2-epitope (PQPELPYPQPQL (SEQ ID NO: 3)) (both from Research Genetics). The final peptide-concentration was 10 µM. T-cell proliferation was assessed by thymidine incorporation (Molberg et al. supra). TCC were identified as peptide-specific by a stimulation index (counts per minute (cpm)) after antigen stimulation/cpm after medium stimulation) above three.

Statistical Analysis

GraphPad Prism 5 software (San Diego, Calif.) was used for statistical analysis and the Mann-Whitney U test to calculate statistical significance.

Results

Visualizing Gluten-specific T Cells in Peripheral Blood

Figure 4:
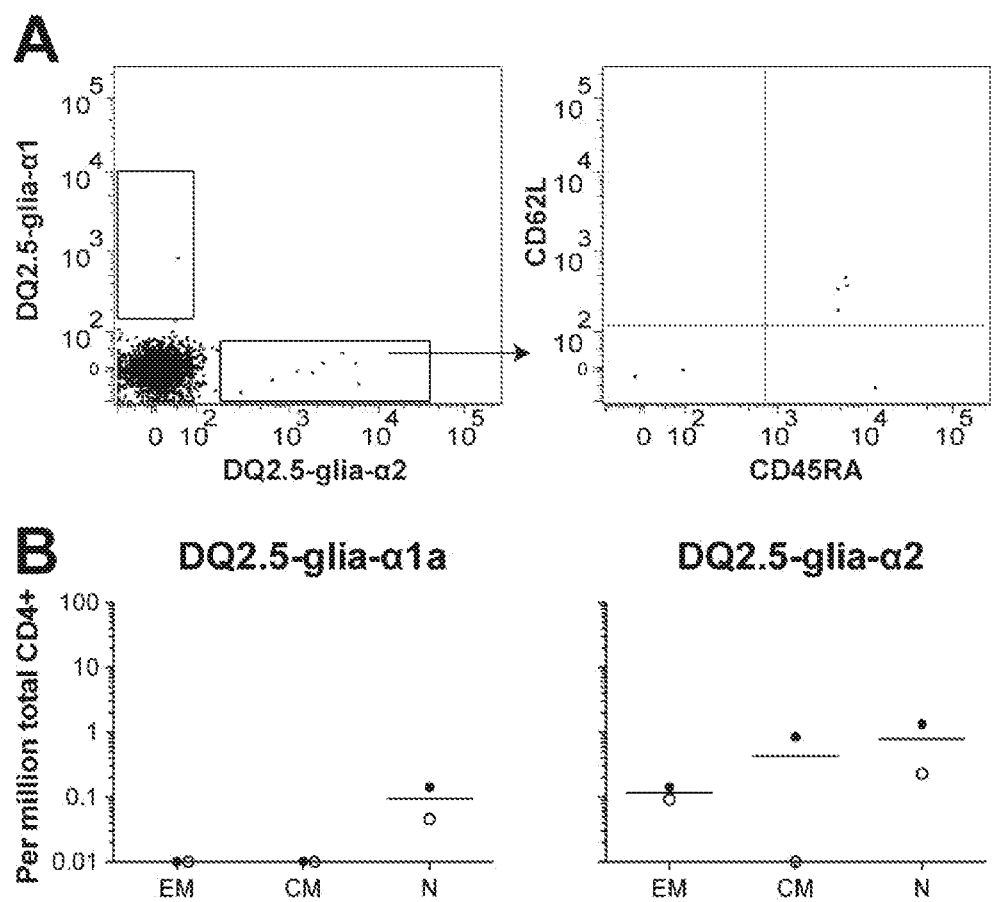
FIG. 4 shows (A) DQ2.5 tetramer-binding CD4+ T cells in an HLA-DQ8+ TCD. (B) Prevalence of CD4+DQ2.5 tetramer-binding $T_{EM}$, $T_{CM}$ and $T_N$ in an HLA-DQ8+ TCD (open circle) and in an HLA-DQ2.2+UCD. Frequencies below <0.01 per million are placed on the x-axis for visualization purposes.

CD4+ $T_N$ specific for the two dominant gluten-epitopes DQ2.5-glia-α1a and DQ2.5-glia-α2 in DQ2.5+ controls were identified. As the frequency of gluten-specific CD4+ $T_N$ was expected to be low, buffy coat of lymphocytes was used. False positive tetramer-binding was excluded by excluding CD11c+, CD14+, CD19+ and CD56+ cells (FIG. 1A). A strict gating was used for identification of sub-populations of CD4+ tetramer-binding T cells (FIG. 1B). Little tetramer-staining was observed among CD3+CD4− T cells (FIG. 1A). By contrast, some tetramer-binding CD4+ T cells were found in non-HLA-DQ2.5 subjects (FIGS. 4A and B) similar to what has been seen with other MHC II tetramers (Legoux et al., J Immunol 2010; 184:6731-8; Kwok et al., J Immunol 2012; 188:2537-4). In all but one control, a population of tetramer-positive CD4+ $T_N$ and relatively few $T_{CM}$ or $T_{EM}$ was identified.

A large number of tetramer-binding CD4+ $T_{EM}$ was detected in control participant no. 2 (P2). This finding implied that P2 had an expansion of gluten-specific $T_{EM}$, indicating that he or she might have an untreated and undiagnosed CD. The buffy coats were collected anonymously from the blood bank precluding clinical examination of the donors. These subjects were all included in the group of control individuals.

Based on the successful visualization of gluten-specific T cells in controls, the study was extended to include TCD and UCD diagnosed according to statements from the American Gastroenterological Association (AGA Institute Medical Position Statement on the Diagnosis and Management of Celiac Disease. Gastroenterology 2006; 131:1977-80) (Table 1).

Validating the Gluten Specificity of Tetramer-binding T Cells

Tetramer-binding CD4+ $T_N$, and in some cases also $T_{EM}$ and $T_{CM}$ from six controls, two UCD and five TCD were sorted, cloned by limited dilution and cultured in an antigen-independent manner. The success rate of generating T-cell clones (TCC) from sorted T cells differed greatly between the subjects. In average, growing TCC was cultured from ¼ of sorted cells (Table 2). Each generated TCC was assayed for proliferative response to the DQ2.5-glia-α1a- and the DQ2.5-glia-α2-epitope. It was found that 122/163 $T_{EM}$, 4/20 $T_{CM}$ and 76/193 $T_N$ clones responded to the epitope (stimulation index (SI) above three) of the tetramer for which they originally were isolated. Tetramer-binding $T_{CM}$ and $T_{EM}$ cells from subject P36 were sorted together and 23/30 of these clones were specific in the T cell assay (FIG. 5A). All TCCs that gave specific responses in T-cell assays had a clear and specific staining with the corresponding tetramer. No TCC that was reactive to both gluten-epitopes were generated, but 5 $T_{EM}$ and 30 $T_N$ clones showed poor proliferation (SI<3) despite clear tetramer staining Twelve of the co-sorted $T_{EM}$ and $T_{CM}$ clones from subject P36 also held this feature.

The Frequency of Gluten-specific T Cells in Peripheral Blood

Figure 2:
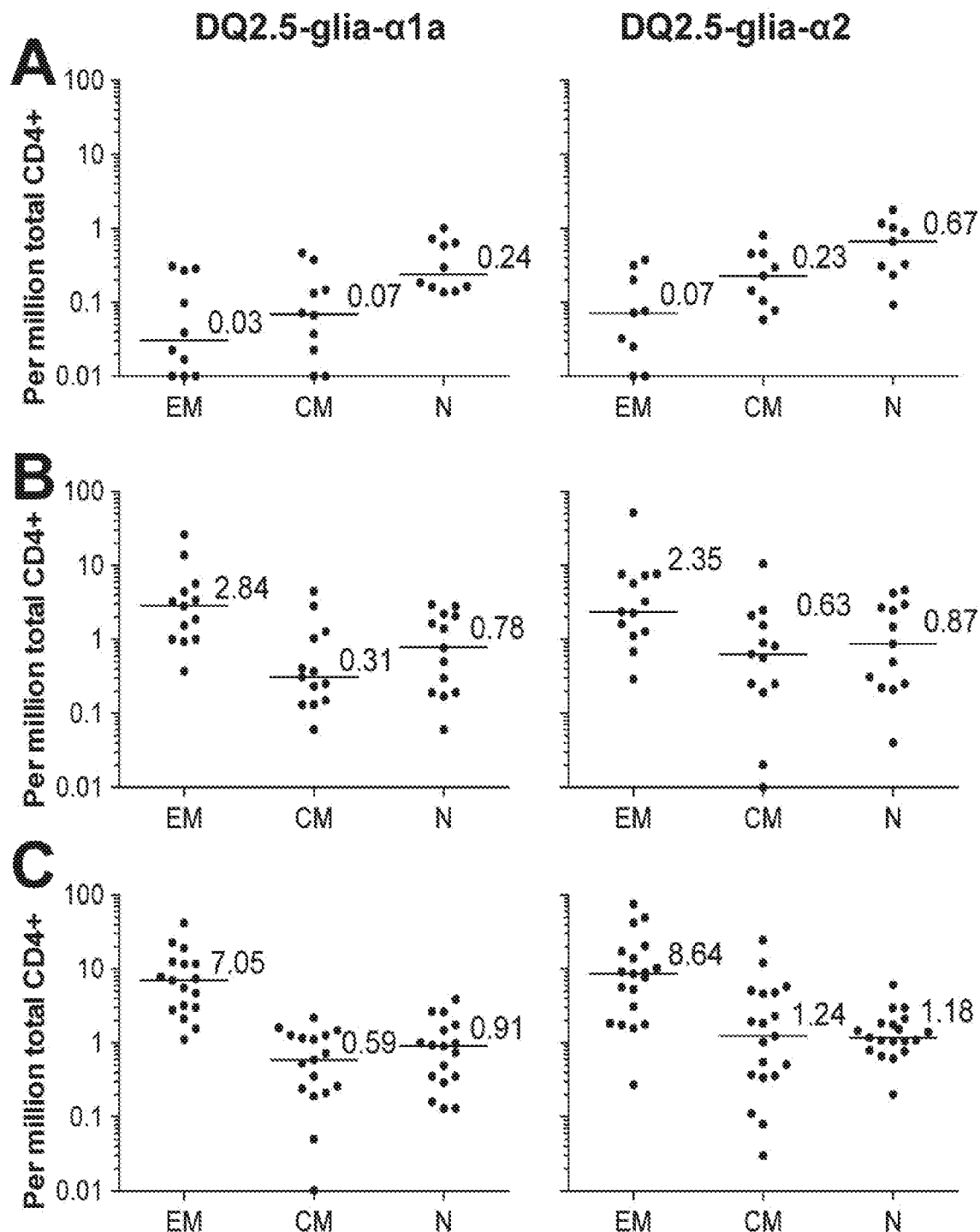
FIG. 2 shows the prevalence of CD4+ T cells binding the DQ2.5-glia-α1a-tetramer (left) and the DQ2.5-glia-α2-tetramer (right) among $T_{EM}$, $T_{CM}$ and $T_N$ per million total CD4+ T cells. Each participant is indicated by a closed circle. The median frequency is denoted with numbers in (A) controls, (B) TCD and (C) UCD. Frequencies below <0.01 per million are placed on the x-axis for visualization purposes.

Tetramer-binding CD4+ $T_N$, $T_{CM}$ and $T_{EM}$ cells were enumerated in controls, TCD and UCD (FIG. 2). The frequency of CD4+ $T_N$ binding the DQ2.5-glia-α1a- and the DQ2.5-glia-α2-tetramer was similar among the three participant groups. The respective median frequency was 0.61 and 0.94 per million total CD4+ T cells for all HLA-DQ2.5+ participants. Similar frequencies of CD4+ $T_{CM}$ binding the DQ2.5-glia-α1a-tetramer (median 0.29 per million CD4+ T cells) and the DQ2.5-glia-α2-tetramer (median 0.49 per million CD4+ T cells) were observed among HLA-DQ2.5+ controls, TCD and UCD.

Figure 3:
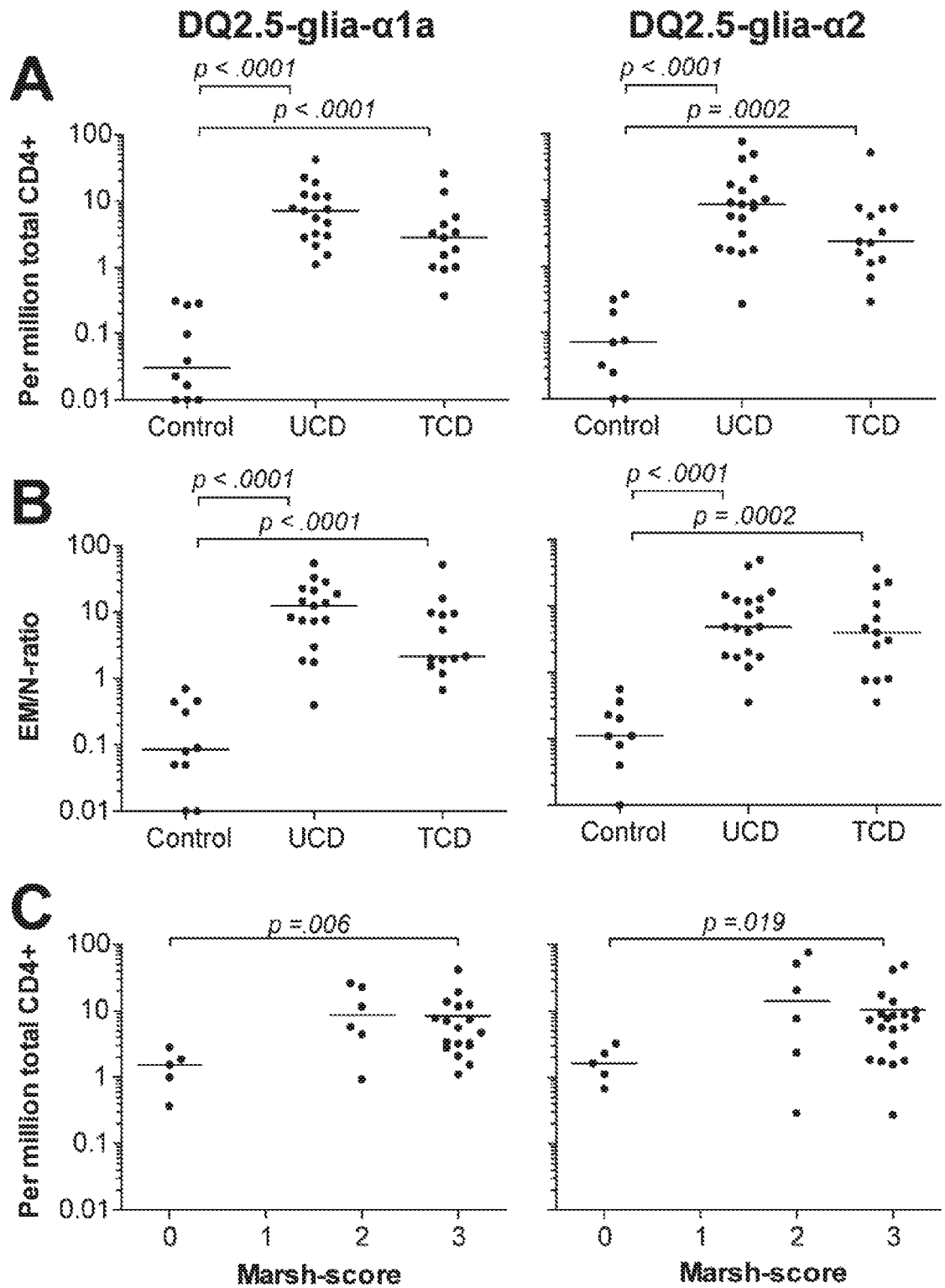
FIG. 3 shows (A) Difference in frequency of CD4+ $T_{EM}$ binding the DQ2.5-glia-α1-tetramer (left) and the DQ2.5-glia-α2-tetramer (right) among controls, UCD and TCD. (B) Ratio between tetramer-binding CD4+ $T_{EM}$ and $T_N$ (EM/N-ratio). Each frequency and ratio is indicated by a closed circle. (C) Correlation between Marsh score and the prevalence of tetramer-binding CD4+ $T_{EM}$ for all participants where duodenal biopsies were obtained.

In contrast, there was a significantly higher frequency of tetramer-binding CD4+ $T_{EM}$ in UCD compared to controls (p<0.0001 for both tetramers) and in TCD compared to controls (p<0.0001 and p=0.0002) (Table 1 and FIG. 3A). Except for subject P2, all control individuals had a frequency of $T_{EM}$ binding either of the tetramer below 0.4 per million total CD4+ T cells. In comparison the prevalence was 1 or above in 18/19 HLA-DQ2.5+UCD and 11/13 HLA-DQ2.5+ TCD.

The EM/N-ratio in Patients and Controls

In order to get a simpler and more robust parameter for the T-cell response to gluten, the number $T_{EM}$ was divided by the number of $T_N$ (termed the EM/N-ratio). This parameter better reflects the phenotypic characteristics of the epitope-specific T-cell response as it is less sensitive to unspecific staining, tetramer concentration and the uncertainty associated with estimating total CD4+ number. For both epitopes studied, significant differences in the EM/N-ratio between controls (all with a ratio <1, except for subject P2) and UCD (all with a ratio >1, except for subject P24) and between controls and TCD (12/13 with a ratio >1 for one or both of the tetramers) was observed (Table 1 and FIG. 3B).

Gluten-specific $T_{EM}$ Versus Duodenal Changes

The histologic appearance in the duodenal mucosa can be characterized by the Marsh-classification (Marsh et al., Clin Gastroenterol 1995; 9:273-93; Oberhuber et al., Eur J Gastroenterol Hepatol 1999; 11:1185-94). Marsh-score 0 corresponds to normal mucosa and score 1 is characterized by increased numbers of intraepithelial lymphocytes. A hyperplastic lesion, further increased number of intraepithelial lymphocytes and crypt hyperplasia are features of Marsh score 2 whereas Marsh score 3 denotes variable degrees of villous blunting. It is poorly understood how histological changes related to gluten-ingestion develop, but gluten-specific CD4+ T cells are thought to play a crucial role (Lundin et al., J Exp Med 1993; 178:187-96; Lundin et al., Hum Immunol 1994; 41:285-91; Molberg et al., Scand J Immunol 1997; 46:103-9).

Variations in the prevalence of gluten-specific CD4+ $T_{EM}$ in peripheral blood correlated to histological changes in the small intestine of all participating TCD and UCD at the time-point of blood-analysis (FIG. 3C). The few obtained frequencies of tetramer-binding cells among patients with Marsh score 2 was wide spread, but there was a significantly higher frequency of DQ2.5-glia-α1a and DQ2.5-glia-α2 specific CD4+ $T_{EM}$ in participants with Marsh score 3 compared to participants with Marsh-score 0.

This experiment demonstrated that gluten-reactive T cells in peripheral blood can be characterized and enumerated directly ex vivo in TCD, UCD and controls. The prevalence of CD4+ $T_{CM}$ and $T_N$ binding the two gliadin epitope-DQ2.5 tetramers was similar in all three participant groups, and the frequency of $T_N$ was within the range of what has been described for naïve CD4+ T cells reactive to other antigens in humans (Kwok et al., J Immunol 2012 188:2537-4). The median number of gluten-specific CD4+ $T_{EM}$ in TCD and UCD was one to two logs higher than in the controls. This is due to an antigen driven T-cell immune response. This response finds use as a diagnostic tool in CD.

The ratio of $T_{EM}/T_N$ cells finds use as a parameter for gluten-dependent expansion of specific T cells. A ratio >1 reflects an immune response to gluten proteins indicative of CD. In fact, all UCD and TCD in this study had either an EM/N-ratio >1 or frequency of $T_{EM}$ specific for one or both of the epitopes DQ2.5-glia-α1a or DQ2.5-glia-α2>1 per million total CD4+ T cells. In comparison, all controls had both EM/N-ratio <0.8 and frequency of specific $T_{EM}$<0.4 per million total CD4+ T cells, except for subject P2. Based on this finding, it is contemplated that P2 has undiagnosed CD.

The GFD will reverse and often normalize diagnose-dependent parameters like disease-specific antibody-titers and histology of the duodenum in CD patients (Sulkanen et al., Gastroenterology 1998; 115:1322-8). Still, TCD follow-up often demonstrates slow and incomplete histological improvement in many patients (Wahab et al., Am J Clin Pathol 2002; 118:459-630). Further, presence of activated CD4+ T cells in the lamina propria and ongoing proliferation of intraepithelial lymphocytes have been reported in TCD (Halstensen et al., Eur J Immunol 1993; 23:505-10; Olaussen et al., Gastroenterology 2007; 132:2371-82). Duodenal TG2-specific antibody-secreting cells can be detected in some and duodenal gluten-specific T cells in the majority of TCD (Di Niro et al., Nat Med 2012; 18:441-5; Lundin e al., J Exp Med 1993; 178:187-96). Together, these data indicate a persistent immune response to gluten in several TCD. This is supported by results in the present study as measurable T-cell responses to gluten were observed in PBMC from all included TCD despite normal mucosa and negative antibody-responses in many of them.

A measurable T-cell response to gluten in TCD may represent long-lived memory T-cells similar to pathogen-specific T-cell responses after acute infections (Harrington et al., Nature 2008; 452:356-60; Pepper et al., Nat Immunol 2010; 11:83-9). Local IL-15 production may contribute to this persistent immune response (Meresse et al., Immunity 2004; 21:357-366). In addition, a continuous immune-response to gluten may reflect sporadic exposure to small amounts of antigen.

The connection between the frequency of tetramer+$T_{EM}$ cells in blood and the histological architecture in the small intestine is notable. Although gluten-specific T cells are not responsible for the remodeling of the intestinal mucosa directly, they can drive inflammation through pro-inflammatory mediators that activate intraepithelial cytotoxic T lymphocytes (Bodd et al., Mucosal Immunol 2010; 3:594-601; Jabri et al., Nat Rev Immunol 2009; 9:858-70). A statistical significant difference in $T_{EM}$ between CD patients with Marsh score 0 and CD patients with Marsh score 3 was observed. Gluten-dependent intestinal changes can be patchy and biopsies from one and the same patient can show variable histological changes (Green, Gastrointest Endosc 2008; 67:1088-90; Pais et al., Gastrointest Endosc 2008; 67:1082-7; Weir et al., Am J Gastroenterol 2010; 105:207-12).

In control subjects some $T_{EM}$ and $T_{CM}$ that stained with the two gliadin epitope-DQ2.5 tetramers were detected. These cells may have differentiated not by gluten-antigen stimulation but rather by homeostatic signals from self-peptides (Haluszczak et al., The Journal of Experimental Medicine 2009; 206:435-448; Akue et al., J Immunol 2012; 188:2516-23; Rudd et al., Proc Natl Acad Sci USA 2011; 108:13694-9; Su et al., Immunity 2013; 38:373-83) or by cross-reactivity to other exogenous antigens as it has been demonstrated that adults have tetramer staining memory CD4+ T specific cells staining with epitopes of viruses they never have been exposed to (Su et al., supra). The cells may have been primed against gluten, and their presence could indicate a T-cell response to gluten without development of celiac disease.

The diagnosing of celiac disease is based on some of its autoimmune features (Sollid et al., Curr Opin Immunol 2005; 17:595-600) and the diagnostic approach can be difficult. Some patients present with histological changes in the small intestine but negative serology (Dickey et al., Scand J Gastroenterol 2000; 35:181-3). Others present with positive serology without intestinal changes, but will fulfill the diagnostic criteria after repeated gastroduodenoscopies (Marsh, Gastroenterology 1992; 102:330-54). Still, these individuals benefit from a GFD at an earlier stage (Kurppa et al., Gastroenterology 2009; 136:816-23). This has led to an ongoing debate on the diagnostic criteria for CD (Kurppa et al., supra; Kaukinen et al., Dig Dis Sci 2001; 46:879-87). A significant difference in the number of gluten-specific $T_{EM}$ in UCD and TCD compared to controls was observed. As these cells are thought to be key pathogenic players and constitute a direct response to gluten, this ex-vivo-based method is useful in the diagnosis of the disease. It is a new diagnostic approach that is useful in patients with vague diagnostic conditions, in cases where a gastroduodenoscopy is inappropriate or undesirable and also in diagnostic routine work.

TABLE 1

Characteristics of participants

| Participant | Category* | HLA-type | Anti-TG2 <5 U/mL** | Marsh-score | EM/N-ratio α1a | EM/N-ratio α2 |
|---|---|---|---|---|---|---|
| P1 | Control | DQ2.5 | ND | ND | 0.0 | 0.2 |
| P2 | Control | DQ2.5 | ND | ND | 6.8**** | |
| P3 | Control | DQ2.5 | ND | ND | 0.1 | 0.1 |
| P4 | Control | DQ2.5 | ND | ND | 0.1**** | |
| P5 | Control | DQ2.5 | ND | ND | 0.1 | ND |
| P6 | Control | DQ2.5 | ND | ND | 0.5 | 0.6 |
| P7 | Control | DQ2.5 | ND | ND | 0.0 | 0.0 |
| P8 | Control | DQ2.5 | ND | ND | 0.7 | 0.1 |
| P9 | Control | DQ2.5 | ND | ND | 0.1 | 0.2 |
| P10 | Control | DQ2.5 | ND | ND | 0.1 | 0.4 |
| P11 | Control | DQ2.5/DQ8 | <0.1 | 1 | 0.4 | 0.0 |
| P12 | Control | DQ2.5/DQ8 | <0.1 | 1 | 0.3 | 0.0 |
| P13 | UCD | DQ2.5/DQ8 | 10.6 | 3B | 21.0 | 4.1 |
| P14 | UCD | DQ2.5 | 16.3 | 3B | 14.5 | 4.9 |
| P15 | UCD | DQ2.5 | 10.0 | 3A | 6.8 | 1.0 |
| P16 | UCD | DQ2.5/DQ8 | >120 | 3B | 13.2 | 4.6 |
| P17 | UCD | DQ2.5 | 12.5 | 3A/B | 18.8 | 1.7 |
| P18 | UCD | DQ2.5 | 48.0 | 3A | 55.0 | 40.0 |
| P19 | UCD | DQ2.5 | 67.0 | 3B/C | 7.3 | 4.7 |
| P20 | UCD | DQ2.5 | 3.3 | 3A | ND | 7.3 |
| P21 | UCD | DQ2.5 | ND | 3A | ND | 12.8 |
| P22 | UCD | DQ2.5 | ND | 2 | 22.6 | 49.5 |
| P23 | UCD | DQ2.5 | 16.4 | 3A | 2.3 | 1.7 |
| P24 | UCD | DQ2.5 | 5.4 | 3B-C*** | 0.4 | 0.4 |
| P25 | UCD | DQ2.5 | 3.8 | 3C | 1.8 | 2.0 |
| P26 | UCD | DQ2.5/DQ8 | 4.8 | 3B | 1.9 | 1.8 |
| P27 | UCD | DQ2.5 | 11.0 | 3B | 13.7 | 12.2 |
| P28 | UCD | DQ2.5 | 35.7 | 2 | 33.0 | 11.7 |
| P29 | UCD | DQ2.5 | 5.7 | 3A | 28.5 | 16.3 |
| P30 | UCD | DQ2.5 | 3.1 | 3B | 7.5 | 8.8 |
| P31 | UCD | DQ2.5 | 2.2 | 3A | 7.6 | 14.4 |
| P32 | TCD | DQ2.5 | 3.3 | 3B | 1.5 | 3.0 |
| P33 | TCD | DQ2.5 | 1.2 | 0 | 0.7 | 0.4 |
| P34 | TCD | DQ2.5 | 1.1 | 0 | 2.0 | 0.8 |
| P35 | TCD | DQ2.5 | 2.1 | 2 | 15.9 | 19.3 |
| P36 | TCD | DQ2.5 | ND | 3A | 52.0 | 22.8 |
| P37 | TCD | DQ2.5 | <1.0 | ND | 5.3 | 4.0 |
| P38 | TCD | DQ2.5 | <1.0 | 2 | 2.1 | 10.7 |
| P39 | TCD | DQ2.5/DQ8 | <1.0 | 3A | 9.8 | 36.3 |
| P40 | TCD | DQ2.5 | <1.0 | 0 | 9.0 | 4.7 |
| P41 | TCD | DQ2.5 | <1.0 | 0 | 9.5 | 0.8 |
| P42 | TCD | DQ2.5 | ND | 2 | 1.2 | 6.5 |
| P43 | TCD | DQ2.5 | <1.0 | 0 | 2.0 | 0.8 |
| P44 | TCD | DQ2.5 | ND | 2 | 1.9 | 2.6 |
| P45 | TCD | DQ8 | 1.1 | 3A | 0.0 | 0.4 |
| P46 | UCD | DQ2.2 | <1.0 | 3A/B | 0.0 | 0.1 |
| P47 | Control | DQ2.5 | ND | ND | 0.3**** | |
| P48 | Control | DQ2.5 | ND | ND | 0.2**** | |
| P49 | Control | DQ2.5 | ND | ND | 0.4**** | |
| P50 | Control | DQ2.5 | ND | ND | 0.4**** | |
| P51 | TCD | DQ2.5 | <1.0 | 0 | 1.7**** | |
| P52 | TCD | DQ2.5 | 1.4 | ND | 0.3**** | |
| P53 | TCD | DQ2.5 | <1.0 | 0 | 9.9**** | |
| P54 | TCD | DQ2.5 | <1.0 | 2 | 2.8**** | |

The ratio between tetramer-binding CD4+ $T_{EM}$ cells and $T_N$ cells (EM/N-ratio) is shown for each participant.
*Patients P1-P10 were anonymous blood bank donors.
**UCD were usually referred to gastroduodenoscopy with IgA anti-TG2 above cut-off. These values refer to the repeated sample at time of endoscopy.
***The mucosal changes were only asserted in bulbus duodeni in this participant.
****The gliadin tetramer-staining was combined on one fluorochrome.
ND: Not done

TABLE 2

The specificity of TCC cultured from tetramer-sorted CD4+ T cells.

| | | Cultured TCC (%) | | | Specific/Proliferating TCC | | |
|---|---|---|---|---|---|---|---|
| Participant | Category | EM | CM | n | EM | CM | n |
| P1 | Control | ND | ND | 27 | ND | ND | 24/30 |
| P2 | Control | ND | ND | 32 | ND | ND | 20/24 |
| P3 | Control | ND | ND | 41 | ND | ND | 30/32 |
| P4 | Control | ND | ND | 31 | ND | ND | 13/13 |
| P8 | Control | 33 | 25 | 62 | 0/4 | 2/6 | 3/29 |
| P11 | Control | 0 | ND | 42 | 0/0 | ND | 2/8 |
| P13 | UCD | 3 | ND | 11 | 4/4 | ND | 1/1 |
| P14 | UCD | 23 | ND | 43 | 70/72 | ND | 8/13 |
| P32 | TCD | 20 | ND | 32 | 7/8 | ND | 3/9 |
| P33 | TCD | 33 | ND | 8 | 1/2 | ND | 2/2 |
| P36 | TCD | 21* | | 50 | 35/39* | | 0/1 |
| P38 | TCD | 16 | 17 | 52 | 7/15 | 0/3 | 0/17 |
| P39 | TCD | 33 | 16 | 18 | 38/58 | 2/11 | 0/16 |

The percentage of sorted T cells surviving the antigen independent cloning and the number of specific T-cell clones (TCC) as defined by specific re-staining, of the total number of growing TCC, are shown.
CD4+ T cells binding the DQ2.5-glia-α1a- or the DQ2.5-glia-α2-tetramer are merged in this table.
*$T_{EM}$ and $T_{CM}$ were sorted into one tube.

TABLE 3

Tetramers

| | |
|---|---|
| DQ2.5-glia-α1a | RDSGQLQPFPQPELPYGAGSLVPR (SEQ ID NO: 4) |
| DQ2.5-glia-α2 | RDSGPQPELPYPQPEGAGSLVPR (SEQ ID NO: 5) |
| DQ2.5-glia-γ1 | RDSGPEQPQQSFPEQERPGAGSLVPR (SEQ ID NO: 6) |
| DQ2.5-glia-γ2 | RDSGQGIIQPEQPAQLGAGSLVPR (SEQ ID NO: 7) |
| DQ2.5-glia-γ3 | RDSGFPEQPEQPYPEQGAGSLVPR (SEQ ID NO: 8) |
| DQ2.5-glia-γ4c | RDSGTEQPEQPFPQPGAGSLVPR (SEQ ID NO: 9) |
| DQ2.5-glia-ω1 | RDSGQQPFPQPEQPFPGAGSLVPR (SEQ ID NO: 10) |
| DQ2.5-glia-ω2 | RDSGFPQPEQPFPWQPGAGSLVPR (SEQ ID NO: 11) |

Control tetramer

| | |
|---|---|
| DQ2.5-CLIP2 | RDSGMATPLLMQALPMGALGAGSLVPR (SEQ ID NO: 12) |

Example 2

Gut Homing of Gluten-specific $T_{EM}$

Figure 6:
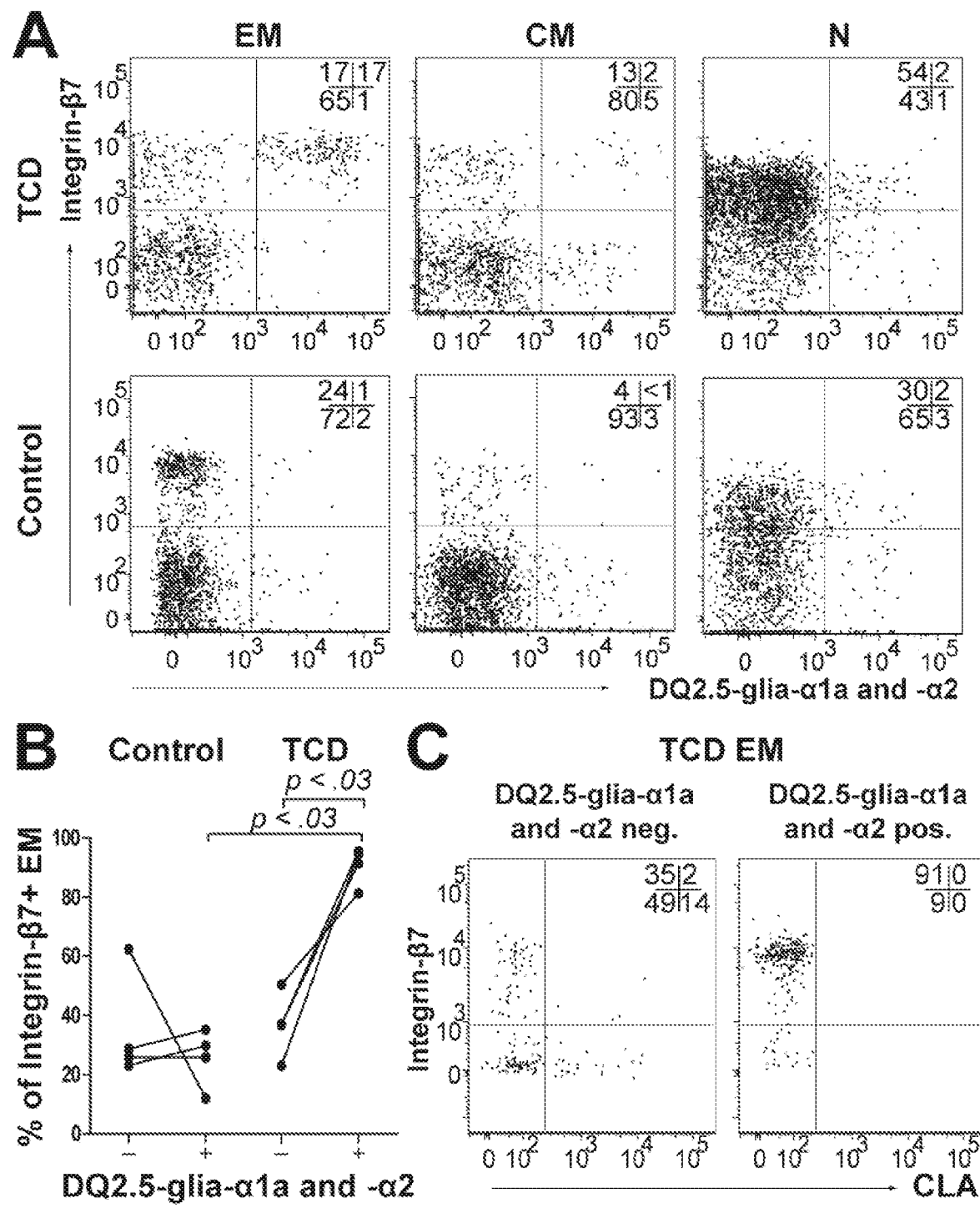
FIG. 6 shows gut-homing of T cells. (A) While gliadin-tetramer positive and negative naïve T cells (N) expressed integrin-β7 at intermediate levels and central memory T cells (CM) showed no clear staining, nearly all gliadin-tetramer+ effector memory (EM) in treated celiac disease patients (TCD) expressed integrin-β7. (B) The percent of integrin-β7 expression on tetramer-positive and tetramer-negative cells in 4 TCD and 4 controls. (C) Tetramer+$T_{EM}$ in one tested TCD did not express the skin-homing cutanous leucocyte-associated antigen (CLA). Numbers denote percentages of gated cells within each plot.

A few CD patients had either frequencies of gliadin-tetramer+$T_{EM}$ or an EM/N-ratio similar to controls. To test whether patients and controls could be further distinguished, CD4+ gliadin-tetramer positive versus negative cells in four TCD and four controls were analyzed for the gut-homing marker integrin-β7 in the population of cells obtained after tetramer bead enrichment (FIGS. 6A-B), using Integrin-β7-PE as fluorochrome-labeled antibody. In TCD, significantly more gliadin-tetramer+$T_{EM}$ (80-95%) compared to gliadin-tetramer-cells expressed integrin-β7. In contrast, the integrin-β7 expression did not exceed background in gliadin-tetramer+$T_{EM}$ of controls.

Integrin-β7 forms gut-homing dimers with α4- or $α_E$-sub-units and a skin-homing dimer with the α1 chain. Peripheral blood from one TCD was stained for the cutanous leucocyte-associated antigen (CLA), using the antibody CLA-FITC. None of the gliadin-tetramer+$T_{EM}$ in this TCD expressed the skin-homing marker (FIG. 6C), indicating that the observed integrin-β7 expression is associated with gut-homing rather than skin-homing.

Gut-homing gliadin-tetramer+CD4+ $T_{EM}$ were significantly more frequent in CD patients than controls. These cells reflect an antigen-driven, CD-associated T-cell response. The combination of integrin-β7+ $T_{EM}$ percentage with the EM/N-ratio gave a good discrimination of patients versus controls without performing gluten-challenge.

Example 3

DQ2.2 and DQ8 Epitopes

Additional patient and control samples were tested with DQ2.2 (Table 4) and DQ8 (Table 5) tetramers. Soluble, biotinylated DQ2.2 (DQA1*02:01, DQB1*02:02) molecules were linked with the novel gluten-derived T-cell epitopes DQ2.2-glia-α1 (QAQGSVQPQELPQF (SEQ ID NO: 13)) and DQ2.2-glia-α2 (QPQYSQPEQPIS (SEQ ID NO: 14)) and DQ2.2-glut-L1 (QPPFSEQEQPVLP (SEQ ID NO: 15)) (Sollid et al., Immunogenetics 64: 455-460), essentially as described for DQ2.5 tetramers in Example 1. Likewise, soluble, biotinylated DQ8 (DQA1*03, DQB1*03:02) molecules were linked with the previously described gluten-derived T-cell epitopes DQ8-glia-α1 (SG EGSFQPSQENP (SEQ ID NO: 16)), DQ8-glia-γ1b (FP EQPEQPYPEQ (SEQ ID NO: 17)) and DQ8-glia-γ1a (PQP EQPEQPFPQPQ (SEQ ID NO: 18)) (Sollid et al., *Immunogenetics* 2012 64: 455-460). Integrin-β7-staining was also performed for all samples stained with DQ2.2- and DQ8-tetramers, as described for DQ2.5 tetramers in Example 2.

Figure 7:
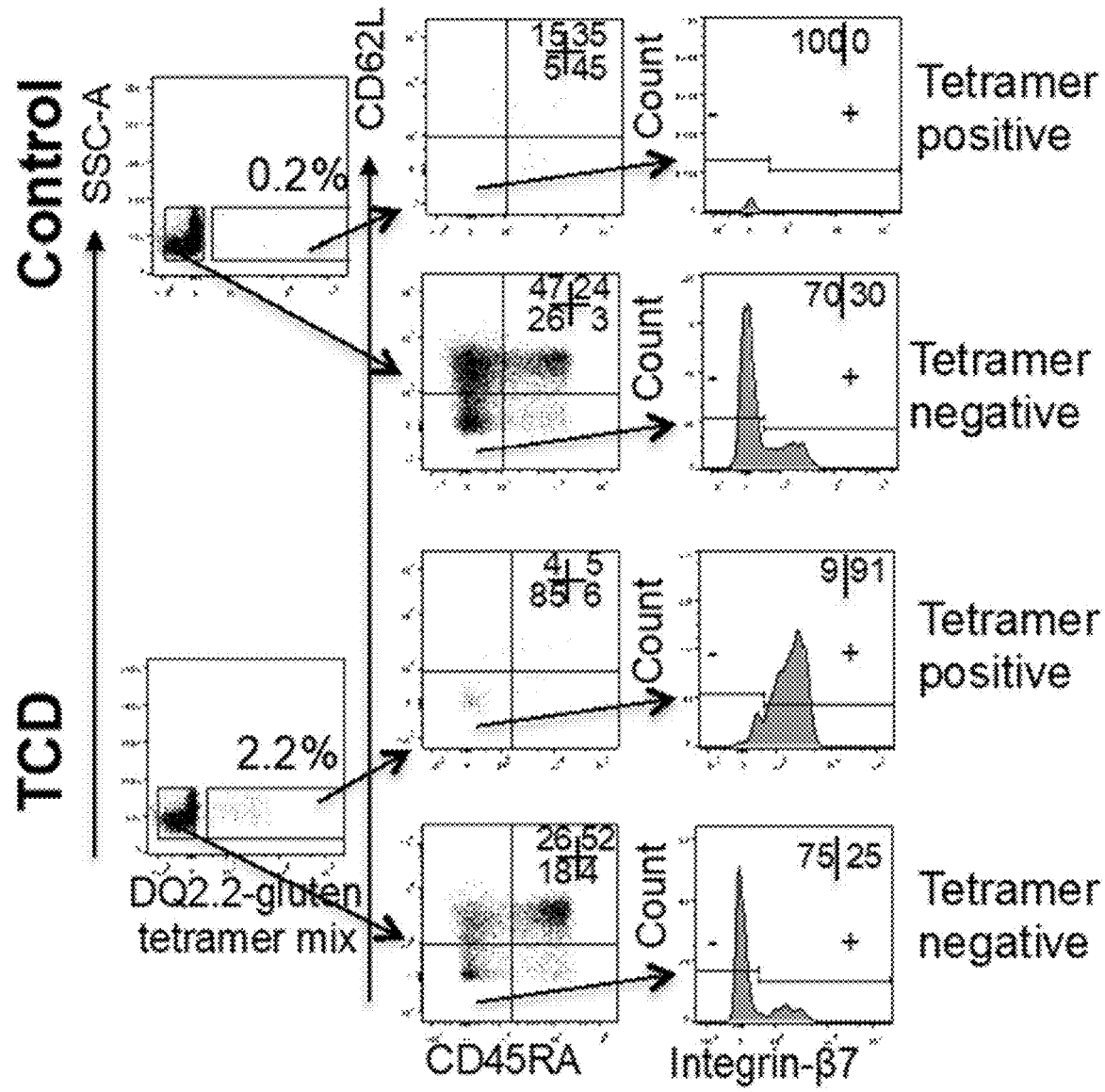
FIG. 7 show CD4+ T cells that were divided into a DQ2.2 tetramer positive and tetramer negative population (left plot). These cell populations were further subdivided by CD62L– and CD45RA-staining into $T_{EM}$ cells (double negative), $T_N$ (double positive), $T_{CM}$ (CD62L+ and CD45RA-). The plots in the right column show the integrin-β7 expression among $T_{EM}$, both among tetramer positive and tetramer negative cells. Tetramer-binding cells were identified in HLA-DQ2.2+ controls and treated CD patients (TCD). Numbers denote percentages of gated cells within each plot.
Figure 8:
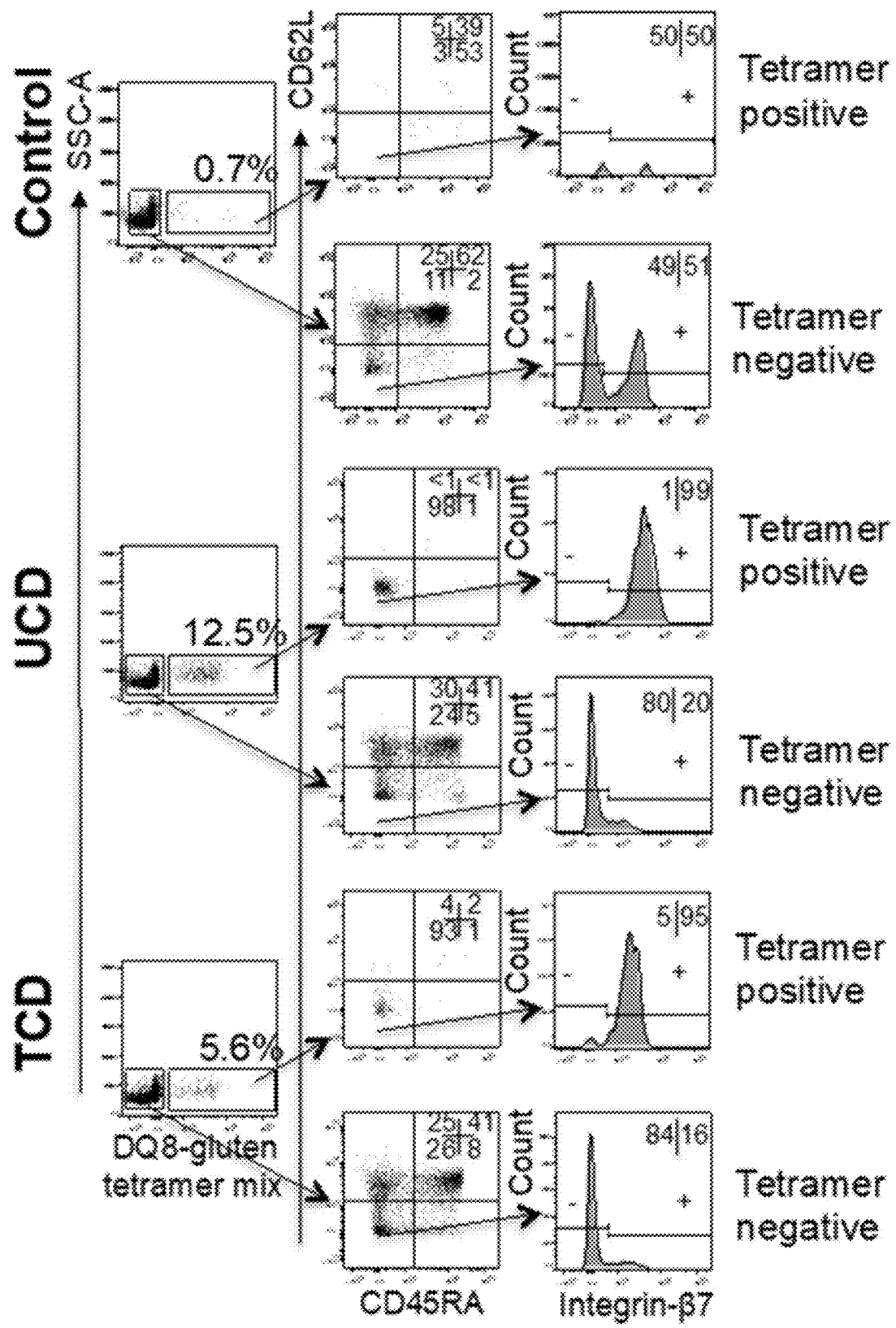
FIG. 8 shows CD4+ T cells that were divided into a DQ8 tetramer positive and tetramer negative population (left plot). These cell populations were further subdivided by CD62L– and CD45RA-staining into $T_{EM}$ cells (double negative), $T_N$ (double positive), $T_{CM}$ (CD62L+ and CD45RA-). The plots in the right column show the integrin-β7 expression among $T_{EM}$, both among tetramer positive and tetramer negative cells. Tetramer-binding cells were identified in HLA-DQ8+ controls, untreated (UCD) and treated CD patients (TCD). Numbers denote percentages of gated cells within each plot.

A significant difference in the EM/N-ratio was observed between CD patients (all with a ratio far above 1) and controls (all with a ratio <1) in individuals with these HLA-types (Tables 4 and 5 and FIGS. 7 and 8) comparable to that observed for DQ2.5 individuals. Furthermore, as for DQ2.5 individuals, a strong increase in the level of integrin-β7 expressing tetramer positive $T_{EM}$ cells in patients (>90%) compared to control individuals (50% or less) for both DQ2.2 and DQ8 HLA subtypes was observed (FIGS. 7 and 8).

The above results demonstrate the general applicability of the diagnostic method for all CD-associated HLA subtypes.

TABLE 4

Characteristics of participants tested with DQ2.2 tetramers

| Participant | Category* | HLA type | Anti-TG2 <5 U/mL* | Marsh-score | EM/N-ratio DQ2.2 tetramer+ cells | % of integrin-β7+ tetramer+ EM cells |
|---|---|---|---|---|---|---|
| P55 | TCD | DQ2.2 | ND | ND | 35 | 94 |
| P56 | TCD | DQ2.2 | ND | ND | 17 | 91 |
| P57 | TCD | DQ2.2 | <1.0 | ND | 17 | 94 |

TABLE 4-continued

Characteristics of participants tested with DQ2.2 tetramers

| Participant | Category* | HLA type | Anti-TG2 <5 U/mL* | Marsh-score | EM/N-ratio DQ2.2 tetramer+ cells | % of integrin-β7+ tetramer+ EM cells |
|---|---|---|---|---|---|---|
| P58 | Control | DQ2.2 | <1.0 | 0 | 0 | 0 |
| P59 | Control | DQ2.2 | <1.0 | 0 | 0.1 | 0 |

The ratio between gliadin-tetramer+ CD4+ effector memory T cells ($T_{EM}$) and naive T cells ($T_N$) (EM/N-ratio) is shown for each participant.
*UCD were usually referred to gastroduodenoscopy with IgA anti-TG2 above cut-off. These values refer to the repeated sample if analyzed at time of endoscopy.
ND: Not done.

TABLE 5

Characteristics of participants tested with DQ8 tetramers

| Participant | Category* | HLA type | Anti-TG2 <5 U/mL** | Marsh-score | EM/N-ratio DQ8 tetramer+ cells | % of integrin-β7+ tetramer+ EM cells |
|---|---|---|---|---|---|---|
| P60 | UCD | DQ8 | >100 | 3B | 185 | 99 |
| P61 | TCD | DQ8 | <1.0 | ND | 72 | 97 |
| P62 | TCD | DQ8 | <1.0 | ND | 61 | 95 |
| P63 | Control | DQ8 | <1.0 | ND | 0.1 | 50 |
| P64 | Control | DQ8 | <1.0 | ND | 0.3 | 50 |

The ratio between gliadin-tetramer+ CD4+ effector memory T cells ($T_{EM}$) and naive T cells ($T_N$) (EM/N-ratio) is shown for each participant.
*UCD were usually referred to gastroduodenoscopy with IgA anti-TG2 above cut-off. These values refer to the repeated sample if analyzed at time of endoscopy.
ND: Not done.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A method of identifying a gluten specific T-cell response, comprising:
   a) contacting a blood sample containing CD4+ from a subject that has not been subjected to a gluten challenge protocol with a multimeric polypeptide comprising a plurality of disease epitope peptides;
   b) enriching CD4+ T cells that bind to the multimeric polypeptide to provide an enriched population of CD4+ T-cells that bind to said disease epitope peptides on said multimeric polypeptide;
   c) separating said enriched population of CD4+ T-cells into Naïve ($T_N$), central memory ($T_{CM}$) and effector memory ($T_{EM}$) CD4+ T– cells and quantifying said $T_N$, $T_{CM}$, and $T_{EM}$ CD4+ T-cells; and
   d) calculation the ratio of CD4+ TEM– cells to CD4+ TN cells;
   e) determining whether the ratio of CD4+ $T_{EM}$– cells to CD4+ $T_N$– cells in said sample is above a pre-determined threshold level indicative of the presence of a gluten-specific T-cell response.

2. The method of claim 1, further comprising the step of separating CD4+ T-cells from said bound T-cells using an antibody specific for CD4+ T-cells to generate disease specific CD4+ T-cells prior to said identifying.

3. The method of claim 2, wherein said steps of separating CD4+ T-cells from said bound T-cells using an antibody specific for CD4+ T-cells and separating said CD4+ T-cells into Naïve ($T_N$), central memory ($T_{CM}$) and effector memory ($T_{EM}$) CD4+ T-cells is done by flow cytometry.

4. The method of claim 1, wherein said ratio is greater than or equal to one.

5. The method of claim 1, wherein said disease epitope is a DQ epitope.

6. The method of claim 5, wherein said DQ epitope is selected from the group consisting of a DQ2 and a DQ8 epitope.

7. The method of claim 6, wherein said DQ2 epitope is a DQ2.5 or DQ2.2 epitope.

8. The method of claim 7, wherein said DQ2.5 epitope is selected from the group consisting of DQ2.5-glia-α1a, DQ2.5-glia-α1b, DQ2.5-glia-α2, DQ2.5-glia-α3, DQ2.5-glia-γ1, DQ2.5-glia-γ2, DQ2.5-glia-γ3, DQ2.5-glia-γ4a, DQ2.5-glia-γ4 b, DQ2.5-glia-γ4c, DQ2.5-glia-γ4d, DQ2.5-glia-γ5, DQ2.5-glia-ω1, DQ2.5-glia-ω2, DQ2.5-glut-L1, DQ2.5-glut-L2, DQ2.5-hor-1, DQ2.5-hor-2, DQ2.5-hor-3, DQ2.5-sec-1, DQ2.5-sec-2, DQ2.5-ave-1 and DQ2.5-ave-2.

9. The method of claim 8, wherein said DQ2.5 epitope is DQ2.5-glia-α1a or DQ2.5-glia-α2.

10. The method of claim 7, wherein said DD2.2 epitope is selected from the group consisting of DQ2.2-glut-L1, DQ2.2-glia-α1 and DQ2.2-glia-α2.

11. The method of claim 6, wherein said DQ8 epitope is selected from the group consisting of DQ8-glia-α1, DQ8-glia-γ1a and DQ8-glia-γ1b and DQ8-glut-H1.

12. The method of claim 1, wherein said multimeric polypeptide is bound to a solid support.

13. The method of claim 12, wherein said disease epitope is present on said solid support as a tetramer.

14. The method of claim 1, further comprising the step of analyzing said CD4+ T-cells for the expression of integrin-β7.

15. A method of characterizing a subject as having a disease related to gluten sensitivity, comprising:
    a) contacting a blood sample containing CD4+ T-cells from a subject that has not been subjected to a gluten challenge protocol with a multimeric polypeptide comprising a plurality of disease epitope peptides, wherein said disease epitope peptides include at least is the DQ2.5 and DQ2.2 epitopes;
    b) enriching CD4+ T-cells that bind to the multimeric polypeptide to provide an enriched population of CD4+ T-cells that bind to said disease epitope peptides on said multimeric polypeptide;
    c) separating said enriched population of CD4+ T-cells into Naïve (TN), central memory (TCM) and effector memory (TEM) CD4+ T-cells and quantifying said TN, TCM, and TEM CD4+ T-cells; and
    d) calculating the ratio of CD4+ TEM¬ cells to CD4+ TN cells; and
    e) characterizing said subject as having said disease related to gluten sensitivity when the ratio of CD4+ TEM¬ cells to CD4+ TN¬ cells is greater than or equal to one in said sample.

16. A method of identifying a gluten-specific T-cell response, comprising:
    a) contacting a blood sample containing CD4+ T-cells from a subject that has not been subjected to a gluten challenge protocol with a multimeric polypeptide comprising a plurality of disease epitope peptides;
    b) enriched CD4+ T-cells that bind to the multimeric polypeptide to provide an enriched population of CD4+ T-cells that bind to said disease epitope peptides on said multimeric polypeptide;
    c) separating said enriched population of CD4+ T-cells into Naïve ($T_N$), central memory ($T_{CM}$) and effector memory ($T_{EM}$) CD4+ T-cells and quantifying said $T_N$, $T_{CM}$, and $T_{EM}$ CD4+ T-cells;
    d) identifying the level of $T_{EM}$ cells positive for integrin-β7 expression; and
    e) calculating the ratio of CD4+ TEM¬ cells to CD4+ TN cells; and
    f) determining whether the ratio of CD4+ $T_{EM}$¬ cells to CD4+ $T_N$¬ cells and/or the level of integrin-β7 expression in said sample is/are above predetermined threshold level(s) and therefore indicative of the presence of a gluten-specific T-cell response.

* * * * *

UNITED STATES PATENT AND TRADEMARK OFFICE
CERTIFICATE OF CORRECTION

PATENT NO. : 10,677,794 B2  
APPLICATION NO. : 14/891001  
DATED : June 9, 2020  
INVENTOR(S) : Sollid et al.

Page 1 of 1

It is certified that error appears in the above-identified patent and that said Letters Patent is hereby corrected as shown below:

In the Claims

In Claim 1, Column 29, Line 56, should read:  
a) contacting a blood sample containing CD4+ T-cells from a In Claim 15, Column 32, Line 12, should read:  
e) characterizing said subject as having a disease In Claim 16, Column 32, Line 22, should read:  
b) enriching CD4+ T-cells that bind to the multimeric In Claim 16, Column 32, Line 38, should read:  
old level(s) and are therefore indicative of the presence of Signed and Sealed this  
Thirteenth Day of October, 2020

Andrei Iancu  
*Director of the United States Patent and Trademark Office*

SEQUENCE LISTING

```
<160> NUMBER OF SEQ ID NOS: 18

<210> SEQ ID NO 1
<211> LENGTH: 12
<212> TYPE: PRT
<213> ORGANISM: Artificial sequence
<220> FEATURE:
<223> OTHER INFORMATION: synthetic

<400> SEQUENCE: 1

Gln Leu Gln Pro Phe Pro Gln Pro Glu Leu Pro Tyr
1               5                   10

<210> SEQ ID NO 2
<211> LENGTH: 11
<212> TYPE: PRT
<213> ORGANISM: Artificial sequence
<220> FEATURE:
<223> OTHER INFORMATION: synthetic

<400> SEQUENCE: 2

Pro Gln Pro Glu Leu Pro Tyr Pro Gln Pro Glu
1               5                   10

<210> SEQ ID NO 3
<211> LENGTH: 12
<212> TYPE: PRT
<213> ORGANISM: Artificial sequence
<220> FEATURE:
<223> OTHER INFORMATION: synthetic

<400> SEQUENCE: 3

Pro Gln Pro Glu Leu Pro Tyr Pro Gln Pro Gln Leu
1               5                   10

<210> SEQ ID NO 4
<211> LENGTH: 24
```

<212> TYPE: PRT
<213> ORGANISM: Artificial sequence
<220> FEATURE:
<223> OTHER INFORMATION: synthetic

<400> SEQUENCE: 4

Arg Asp Ser Gly Gln Leu Gln Pro Phe Pro Gln Pro Glu Leu Pro Tyr
1               5                   10                  15

Gly Ala Gly Ser Leu Val Pro Arg
            20

<210> SEQ ID NO 5
<211> LENGTH: 23
<212> TYPE: PRT
<213> ORGANISM: Artificial sequence
<220> FEATURE:
<223> OTHER INFORMATION: synthetic

<400> SEQUENCE: 5

Arg Asp Ser Gly Pro Gln Pro Glu Leu Pro Tyr Pro Gln Pro Glu Gly
1               5                   10                  15

Ala Gly Ser Leu Val Pro Arg
            20

<210> SEQ ID NO 6
<211> LENGTH: 26
<212> TYPE: PRT
<213> ORGANISM: Artificial sequence
<220> FEATURE:
<223> OTHER INFORMATION: synthetic

<400> SEQUENCE: 6

Arg Asp Ser Gly Pro Glu Gln Pro Gln Gln Ser Phe Pro Glu Gln Glu
1               5                   10                  15

Arg Pro Gly Ala Gly Ser Leu Val Pro Arg
            20                  25

<210> SEQ ID NO 7
<211> LENGTH: 24
<212> TYPE: PRT
<213> ORGANISM: Artificial sequence
<220> FEATURE:
<223> OTHER INFORMATION: synthetic

<400> SEQUENCE: 7

Arg Asp Ser Gly Gln Gly Ile Ile Gln Pro Glu Gln Pro Ala Gln Leu
1               5                   10                  15

Gly Ala Gly Ser Leu Val Pro Arg
            20

<210> SEQ ID NO 8
<211> LENGTH: 24
<212> TYPE: PRT
<213> ORGANISM: Artificial sequence
<220> FEATURE:
<223> OTHER INFORMATION: synthetic

<400> SEQUENCE: 8

Arg Asp Ser Gly Phe Pro Glu Gln Pro Glu Gln Pro Tyr Pro Glu Gln
1               5                   10                  15

Gly Ala Gly Ser Leu Val Pro Arg
            20

<210> SEQ ID NO 9

```
<211> LENGTH: 23
<212> TYPE: PRT
<213> ORGANISM: Artificial sequence
<220> FEATURE:
<223> OTHER INFORMATION: synthetic

<400> SEQUENCE: 9

Arg Asp Ser Gly Thr Glu Gln Pro Glu Gln Phe Pro Gln Pro Gly
1               5                   10                  15

Ala Gly Ser Leu Val Pro Arg
            20

<210> SEQ ID NO 10
<211> LENGTH: 24
<212> TYPE: PRT
<213> ORGANISM: Artificial sequence
<220> FEATURE:
<223> OTHER INFORMATION: synthetic

<400> SEQUENCE: 10

Arg Asp Ser Gly Gln Gln Pro Phe Pro Gln Pro Glu Gln Pro Phe Pro
1               5                   10                  15

Gly Ala Gly Ser Leu Val Pro Arg
            20

<210> SEQ ID NO 11
<211> LENGTH: 24
<212> TYPE: PRT
<213> ORGANISM: Artificial sequence
<220> FEATURE:
<223> OTHER INFORMATION: synthetic

<400> SEQUENCE: 11

Arg Asp Ser Gly Phe Pro Gln Pro Glu Gln Pro Phe Pro Trp Gln Pro
1               5                   10                  15

Gly Ala Gly Ser Leu Val Pro Arg
            20

<210> SEQ ID NO 12
<211> LENGTH: 27
<212> TYPE: PRT
<213> ORGANISM: Artificial sequence
<220> FEATURE:
<223> OTHER INFORMATION: synthetic

<400> SEQUENCE: 12

Arg Asp Ser Gly Met Ala Thr Pro Leu Leu Met Gln Ala Leu Pro Met
1               5                   10                  15

Gly Ala Leu Gly Ala Gly Ser Leu Val Pro Arg
            20                  25

<210> SEQ ID NO 13
<211> LENGTH: 14
<212> TYPE: PRT
<213> ORGANISM: Artificial sequence
<220> FEATURE:
<223> OTHER INFORMATION: synthetic

<400> SEQUENCE: 13

Gln Ala Gln Gly Ser Val Gln Pro Gln Glu Leu Pro Gln Phe
1               5                   10

<210> SEQ ID NO 14
<211> LENGTH: 12
<212> TYPE: PRT
```

```
<213> ORGANISM: Artificial sequence
<220> FEATURE:
<223> OTHER INFORMATION: synthetic

<400> SEQUENCE: 14

Gln Pro Gln Tyr Ser Gln Pro Glu Gln Pro Ile Ser
1               5                   10

<210> SEQ ID NO 15
<211> LENGTH: 13
<212> TYPE: PRT
<213> ORGANISM: Artificial sequence
<220> FEATURE:
<223> OTHER INFORMATION: synthetic

<400> SEQUENCE: 15

Gln Pro Pro Phe Ser Glu Gln Glu Gln Pro Val Leu Pro
1               5                   10

<210> SEQ ID NO 16
<211> LENGTH: 13
<212> TYPE: PRT
<213> ORGANISM: Artificial sequence
<220> FEATURE:
<223> OTHER INFORMATION: synthetic

<400> SEQUENCE: 16

Ser Gly Glu Gly Ser Phe Gln Pro Ser Gln Glu Asn Pro
1               5                   10

<210> SEQ ID NO 17
<211> LENGTH: 12
<212> TYPE: PRT
<213> ORGANISM: Artificial sequence
<220> FEATURE:
<223> OTHER INFORMATION: synthetic

<400> SEQUENCE: 17

Phe Pro Glu Gln Pro Glu Gln Pro Tyr Pro Glu Gln
1               5                   10

<210> SEQ ID NO 18
<211> LENGTH: 14
<212> TYPE: PRT
<213> ORGANISM: Artificial sequence
<220> FEATURE:
<223> OTHER INFORMATION: synthetic

<400> SEQUENCE: 18

Pro Gln Pro Glu Gln Pro Glu Gln Pro Phe Pro Gln Pro Gln
1               5                   10
```